(12) United States Patent
Gnamm et al.

(10) Patent No.: US 9,221,807 B2
(45) Date of Patent: Dec. 29, 2015

(54) SUBSTITUTED PYRIDONES AND PYRAZINONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Christian Gnamm, Biberach an der Riss (DE); Thorsten Oost, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/620,323

(22) Filed: Feb. 12, 2015

(65) Prior Publication Data

US 2015/0239875 A1 Aug. 27, 2015

(30) Foreign Application Priority Data

Feb. 21, 2014 (EP) .................................. 14156159

(51) Int. Cl.
| | | |
|---|---|---|
| *A61K 31/535* | (2006.01) | |
| *C07D 211/20* | (2006.01) | |
| *C07D 413/14* | (2006.01) | |
| *C07D 401/04* | (2006.01) | |
| *C07D 403/04* | (2006.01) | |

(52) U.S. Cl.
CPC ............ *C07D 413/14* (2013.01); *C07D 401/04* (2013.01); *C07D 403/04* (2013.01)

(58) Field of Classification Search
None
See application file for complete search history.

(56) References Cited

FOREIGN PATENT DOCUMENTS

| WO | 2005026124 A1 | 3/2005 |
| WO | WO 2007107706 A2 * | 9/2007 |
| WO | 2010094964 A1 | 8/2010 |
| WO | WO 2010094964 A1 * | 8/2010 |
| WO | 2011039528 A1 | 4/2011 |

OTHER PUBLICATIONS

International Search Report and Written Opinion for corresponding application PCT/EP2015/053309, date of mailing May 8, 2015.

* cited by examiner

*Primary Examiner* — Heidi Reese
(74) *Attorney, Agent, or Firm* — Michael P. Morris; Alan R. Stempel; Philip I. Datlow

(57) ABSTRACT

Substituted 2-pyridones and pyrazinones of formula 1

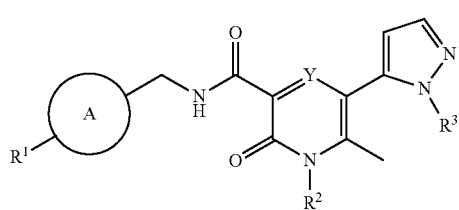

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection and oncological diseases.

9 Claims, No Drawings

SUBSTITUTED PYRIDONES AND PYRAZINONES AND THEIR USE AS INHIBITORS OF NEUTROPHIL ELASTASE ACTIVITY

FIELD OF THE INVENTION

This invention relates to substituted 2-pyridones and pyrazinones of formula 1

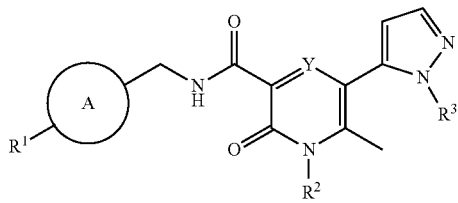

1 and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

BACKGROUND INFORMATION

The following references describe neutrophil elastase inhibitors with a 2-pyridone central core: WO04043924, WO05026123, WO05026124, WO06098683, WO06098684, WO07129962, WO10094964, WO11039528.

The following references describe neutrophil elastase inhibitors with a 2-pyrazinone central core: WO07129963, WO09061271, WO09058076, WO11110852.

The following references describe neutrophil elastase inhibitors with a 4-pyridone central core: WO14029830, WO14029831, WO14029832.

For a review on various inhibitors of neutrophil elastase see: P. Sjo (*Future Med. Chem.* 2012, 4, 651-660).

BRIEF SUMMARY OF THE INVENTION

Neutrophil elastase is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs. Inhibitors of neutrophil elastase will therefore have an important role for the treatment of different diseases like COPD, fibrosis, cancer and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al., J. Pharm. Exp. Ther. 339, 313-320 (2011).

Some compounds according to the present invention, including the physiologically acceptable salts, exhibit favourable in vivo potency, as determined, for example, by the half maximal effective dose (ED50), in models of human neutrophil elastase-induced lung injury in mice, rat or hamster, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di, Drug-like properties: concepts, structure design and methods: from ADME to toxicity optimization, Elsevier, $1^{st}$ ed, 2008, chapter 29 and references therein.

Some compounds according to the present invention, including the physiologically acceptable salts, exhibit favourable metabolic stability in an in vitro hepatocytes assay for metabolic stability as described in E. Kerns & L. Di, Drug-like properties: concepts, structure design and methods: from ADME to toxicity optimization, Elsevier, $1^{st}$ ed, 2008, chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di, Drug-like properties: concepts, structure design and methods: from ADME to toxicity optimization, Elsevier, $1^{st}$ ed, 2008, chapter 26 and references therein. For an oral drug, improved permeability is expected to translate into a higher fraction of the drug absorbed in the intestinal tract, thus, resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability and favourable permeability. Accordingly, some compounds of the present invention are expected to exhibit favourable pharmacokinetic (PK) properties, in particular favourable systemic exposure (area under the curve, AUC).

DETAILED DESCRIPTION OF THE INVENTION

Compounds of formula 1

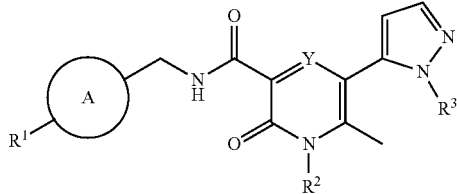

wherein

A is phenyl or a five- or six-membered, aromatic heteroring, wherein one, two or three elements are replaced by an element selected independently from each other from the group consisting of N, (O⁻)—N⁺, O and S; preferably phenyl or pyridyl;

$R^1$ is selected from the group consisting of

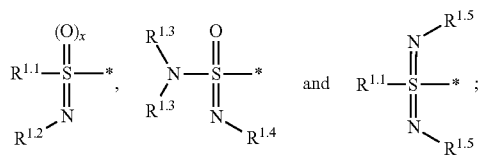

$R^{1.1}$ is selected from the group consisting of $C_{1-4}$-alkyl-, $C_{3-6}$-cycloalkyl- and $C_{1-4}$-haloalkyl-; preferably $C_{1-4}$-alkyl-;

$R^{1.2}$ is selected from the group consisting of H, NC—, $O_2N$—, $C_{1-4}$-alkyl-, $C_{3-6}$-cycloalkyl-, $C_{1-4}$-alkyl-(O)C—, $C_{3-6}$-cycloalkyl-(O)C—, $H_2N$—(O)C—, $C_{1-4}$-alkyl-NH—(O)C—, $C_{3-6}$-cycloalkyl-NH—(O)C—, $C_{1-4}$-alkyl-O—(O)C—, $C_{3-6}$-cycloalkyl-O—(O)C—, $H_2N$—(HO—N)C—, morpholinyl-(O)C— and $C_{1-4}$-alkyl-$SO_2$—, preferably NC—;

or a 5-membered aromatic heterocycle containing one, two or three atoms selected from N, O and S; each ring optionally substituted with one or two residues selected independently from each other from the group consisting of $C_{1-4}$-alkyl-, $C_{3-6}$-cycloalkyl-, halogen and $C_{1-4}$-haloalkyl-;

$R^{1.3}$ is selected from the group consisting of H, $C_{1-4}$-alkyl-, $C_{3-6}$-cycloalkyl-, $C_{1-4}$-alkyl-O—, $C_{3-6}$-cycloalkyl-O—, benzyl-, $H_2N$—, $C_{1-4}$-alkyl-NH— and $(C_{1-4}$-alkyl-$)_2N$—; preferably H and $C_{1-4}$-alkyl-; or two $R^{1.3}$ are together $C_{2-5}$-alkylene forming a carbocyclic heteroring;

$R^{1.4}$ is $C_{1-4}$-alkyl- or $C_{3-6}$-cycloalkyl-; preferably $C_{1-4}$-alkyl-;

$R^{1.5}$ is selected from the group consisting of H, NC—, $C_{1-4}$-alkyl-, $C_{3-6}$-cycloalkyl-, and $C_{1-4}$-alkyl-O—$C_{1-4}$-alkyl-; preferably H and NC—;

x is 0 or 1; preferably 1;

$R^2$ is phenyl or pyridyl, each ring optionally substituted with one or two residues selected independently from each other from the group consisting of $C_{1-4}$-alkyl-, halogen and $C_{1-4}$-haloalkyl-;

$R^3$ is selected from the group consisting of $C_{1-4}$-alkyl-, $C_{3-6}$-cycloalkyl-, $C_{1-4}$-haloalkyl- and $C_{1-4}$-alkyl-O—$C_{1-4}$-alkyl-; preferably $C_{1-4}$-alkyl-;

or phenyl or pyridyl, each ring optionally substituted with one or two residues selected independently from each other from the group consisting of NC—, halogen, $C_{1-4}$-alkyl- and $C_{1-4}$-haloalkyl-;

Y is CH or N;

or a pharmaceutically acceptable salt thereof.

PREFERRED EMBODIMENTS

Preferred are the above compounds of formula 1, wherein A is $A^a$ and $A^a$ is independently selected from phenyl and pyridyl; preferably phenyl.

Preferred are the above compounds of formula 1, wherein Y is $Y^a$ and $Y^a$ is CH.

Preferred are the above compounds of formula 1, wherein Y is $Y^b$ and $Y^b$ is N.

Preferred are the above compounds of formula 1, wherein $R^1$ is $R^{1.a}$ and $R^{1.a}$ is independently selected from

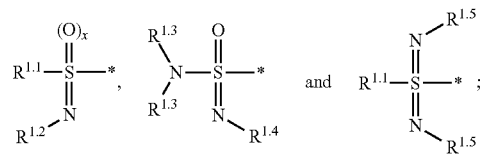

$R^{1.1}$ is selected from the group consisting of $C_{1-4}$-alkyl-, $C_{3-6}$-cycloalkyl- and $C_{1-4}$-haloalkyl-; preferably $C_{1-4}$-alkyl-;

$R^{1.2}$ is selected from the group consisting of H, NC—, $O_2N$—, $C_{1-4}$-alkyl-, $C_{3-6}$-cycloalkyl-, $C_{1-4}$-alkyl-(O)C—, $C_{3-6}$-cycloalkyl-(O)C—, $H_2N$—(O)C—, $C_{1-4}$-alkyl-NH—(O)C—, $C_{3-6}$-cycloalkyl-NH—(O)C—, $C_{1-4}$-alkyl-O—(O)C—, $C_{3-6}$-cycloalkyl-O—(O)C—, $H_2N$—(HO—N)C—, morpholinyl-(O)C— and $C_{1-4}$-alkyl-$SO_2$—, preferably NC—;

or a 5-membered aromatic heterocycle containing one, two or three atoms selected from N, O and S; each ring optionally substituted with one or two residues selected independently from each other from the group consisting of $C_{1-4}$-alkyl-, $C_{3-6}$-cycloalkyl-, halogen and $C_{1-4}$-haloalkyl-;

$R^{1.3}$ is selected from the group consisting of H, $C_{1-4}$-alkyl-, $C_{3-6}$-cycloalkyl-, $C_{1-4}$-alkyl-O—, $C_{3-6}$-cycloalkyl-O—, benzyl-, $H_2N$—, $C_{1-4}$-alkyl-NH— and $(C_{1-4}$-alkyl-$)_2N$—; preferably H and $C_{1-4}$-alkyl-;

or two $R^3$ are together $C_{2-5}$-alkylene forming a carbocyclic heteroring;

$R^{1.4}$ is $C_{1-4}$-alkyl- or $C_{3-6}$-cycloalkyl-; preferably $C_{1-4}$-alkyl-;

$R^{1.5}$ is selected from the group consisting of H, NC—, $C_{1-4}$-alkyl-, $C_{3-6}$-cycloalkyl- and $C_{1-4}$-alkyl-O—$C_{1-4}$-alkyl-; preferably H or NC—;

x is 0 or 1; preferably 1;

Preferred are the above compounds of formula 1, wherein $R^1$ is $R^{1.b}$ and $R^{1.b}$ is independently selected from

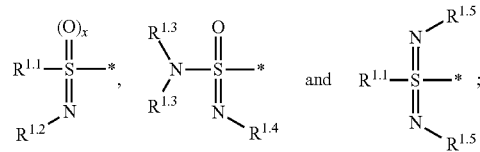

$R^{1.1}$ is $C_{1-4}$-alkyl-;

$R^{1.2}$ is selected from the group consisting of H, NC—, $O_2N$—, $C_{1-4}$-alkyl-, $C_{1-4}$-alkyl-(O)C—, $H_2N$—(O)C—, $C_{1-4}$-alkyl-NH—(O)C—, $C_{1-4}$-alkyl-O—(O)C—, $H_2N$—(HO—N)C—, morpholinyl-(O)C—, $C_{1-4}$-alkyl-$SO_2$— and 4,5-dimethyloxazol-2-yl; preferably NC—;

$R^{1.3}$ is selected from the group consisting of H, $C_{1-4}$-alkyl-, $C_{1-4}$-alkyl-O— and benzyl-; preferably H or $C_{1-4}$-alkyl-; or two $R^{1.3}$ are together $C_{2-5}$-alkylene forming a carbocyclic heteroring;

$R^{1.4}$ is $C_{1-4}$-alkyl-;

$R^{1.5}$ is selected from the group consisting of H, NC—, $C_{1-4}$-alkyl- and $C_{1-4}$-alkyl-O—$C_{1-4}$-alkyl-; preferably H and NC—;

x is 0 or 1; preferably 1;

Preferred are the above compounds of formula 1, wherein $R^1$ is $R^{1.c}$ and $R^{1.c}$ is independently selected from

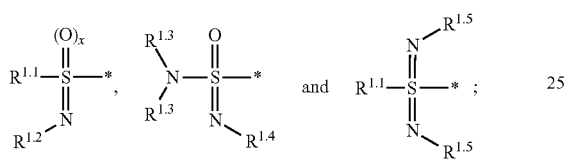

$R^{1.1}$ is methyl;

$R^{1.2}$ is selected from the group consisting of H, NC—, $O_2N$—, methyl, $CH_3$—(O)C—, $H_2N$—(O)C—, $CH_3$—NH—(O)C—, $CH_3$—O—(O)C—, $H_2N$—(HO—N)C—, morpholinyl-(O)C—, $CH_3$—$SO_2$— and 4,5-dimethyloxazol-2-yl;

$R^{1.3}$ is selected from the group consisting of H, methyl, $CH_3$—O— and benzyl-, or two $R^{1.3}$ are together —$(CH_2)_5$—;

$R^{1.4}$ is methyl;

$R^{1.5}$ is selected from the group consisting of H, NC—, methyl and $CH_3$—O—$(CH_2)_2$—;

x is 0 or 1;

Preferred are the above compounds of formula 1, wherein $R^1$ is $R^{1.d}$ and $R^{1.d}$ is independently selected from the group consisting of formulas (a) to (w)

(a) 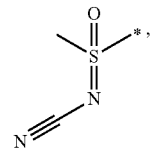

(b) 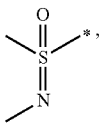

(c) 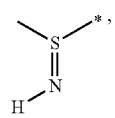

(d) 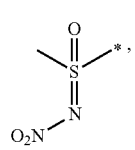

(e) 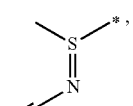

(f) 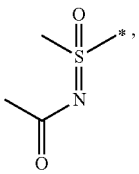

(g) 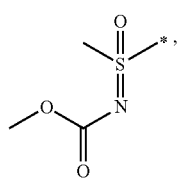

(h) 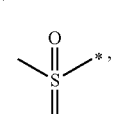

(i) 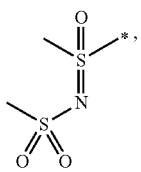

(j) 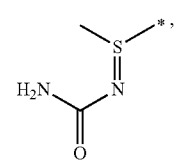

(k) 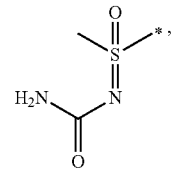

(l) 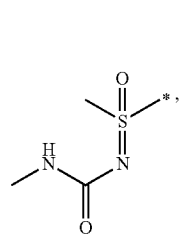

-continued (m) 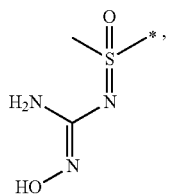

(n) 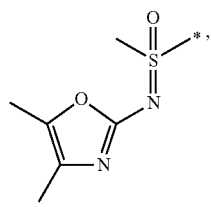

(o) 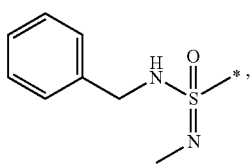

(p) 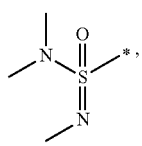

(q) 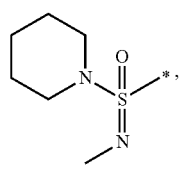

(r) 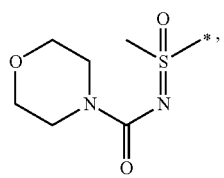

(s) 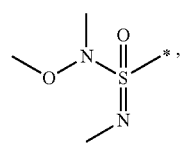

(t) 

(u) 

-continued (v) 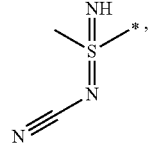

(w) 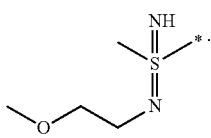

Preferred are the above compounds of formula 1, wherein $R^2$ is $R^{2.a}$ and $R^{2.a}$ is phenyl or pyridyl, each ring optionally substituted with one or two residues selected independently from each other from the group consisting of F, $F_2HC-$ and $F_3C-$.

Preferred are the above compounds of formula 1, wherein $R^2$ is $R^{2.b}$ and $R^{2.b}$ is phenyl or pyridyl, each ring optionally substituted with $F_3C-$.

Preferred are the above compounds of formula 1, wherein $R^2$ is $R^{2.c}$ and $R^{2.c}$ is phenyl, optionally substituted with one or two residues selected independently from each other from the group consisting of halogen and $C_{1-4}$-haloalkyl-; preferably F, $F_2HC-$ and $F_3C-$.

Preferred are the above compounds of formula 1, wherein $R^2$ is $R^{2.d}$ and $R^{2.d}$ is

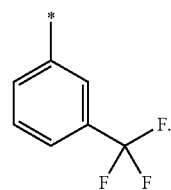 [SMILES: *c1cccc(C(F)(F)F)c1]

Preferred are the above compounds of formula 1, wherein $R^3$ is $R^{3.a}$ and $R^{3.a}$ is independently selected from
$C_{1-4}$-alkyl- and
phenyl, optionally substituted with one or two residues selected independently from each other from the group consisting of NC—, halogen, $C_{1-4}$-alkyl- and $C_{1-4}$-haloalkyl-.

Preferred are the above compounds of formula 1, wherein $R^3$ is $R^{3.b}$, wherein $R^{3.b}$ is independently selected from $C_{1-4}$-alkyl- and 4-cyanophenyl; preferably methyl and 4-cyanophenyl.

Preferred are the above compounds of formula 1, wherein A is phenyl or pyridyl; preferably phenyl;
$R^1$ is selected from the group consisting of

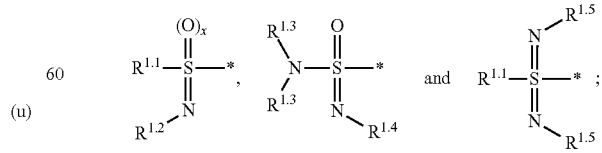

$R^{1.1}$ is selected from the group consisting of $C_{1-4}$-alkyl-, $C_{3-6}$-cycloalkyl- and $C_{1-4}$-haloalkyl-; preferably $C_{1-4}$-alkyl-;

$R^{1.2}$ is selected from the group consisting of H, NC—, $O_2N$—, $C_{1-4}$-alkyl-, $C_{3-6}$-cycloalkyl-, $C_{1-4}$-alkyl-(O)C—, $C_{3-6}$-cycloalkyl-(O)C—, $H_2N$—(O)C—, $C_{1-4}$-alkyl-NH—(O)C—, $C_{3-6}$-cycloalkyl-NH—(O)C—, $C_{1-4}$-alkyl-O—(O)C—, $C_{3-6}$-cycloalkyl-O—(O)C—, $H_2N$—(HO—N)C—, morpholinyl-(O)C— and $C_{1-4}$-alkyl-$SO_2$—, preferably NC—;

or a 5-membered aromatic heterocycle containing one, two or three atoms selected from N, O and S; each ring optionally substituted with one or two residues selected independently from each other from the group consisting of $C_{1-4}$-alkyl-, $C_{3-6}$-cycloalkyl-, halogen and $C_{1-4}$-haloalkyl-;

$R^{1.3}$ is selected from the group consisting of H, $C_{1-4}$-alkyl-, $C_{3-6}$-cycloalkyl-, $C_{1-4}$-alkyl-O—, $C_{3-6}$-cycloalkyl-O—, benzyl-, $H_2N$—, $C_{1-4}$-alkyl-NH— and $(C_{1-4}$-alkyl-$)_2N$—; preferably H and $C_{1-4}$-alkyl-;

or two $R^{1.3}$ are together $C_{2-5}$-alkylene forming a carbocyclic heteroring;

$R^{1.4}$ is $C_{1-4}$-alkyl- or $C_{3-6}$-cycloalkyl-; preferably $C_{1-4}$-alkyl-;

$R^{1.5}$ is selected from the group consisting of H, NC—, $C_{1-4}$-alkyl-, $C_{3-6}$-cycloalkyl- and $C_{1-4}$-alkyl-O—$C_{1-4}$-alkyl-; preferably H or NC—;

x is 0 or 1; preferably 1;

$R^2$ is phenyl or pyridyl, each ring optionally substituted with one or two residues selected independently from each other from the group consisting of F, $F_2HC$— and $F_3C$—;

$R^3$ is $C_{1-4}$-alkyl- or $C_{3-6}$-cycloalkyl-;

or phenyl or pyridyl, each ring optionally substituted with NC— or halogen;

Y is CH or N;

or a pharmaceutically acceptable salt thereof.

Preferred are the above compounds of formula 1, wherein
A is phenyl;
$R^1$ is selected from the group consisting of

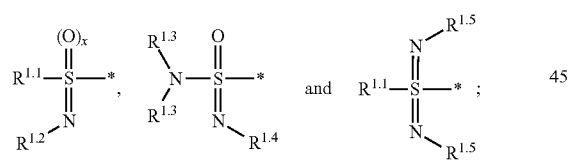

$R^{1.1}$ is $C_{1-4}$-alkyl-;
$R^{1.2}$ is selected from the group consisting of H, NC—, $O_2N$—, $C_{1-4}$-alkyl-, $C_{1-4}$-alkyl-(O)C—, $H_2N$—(O)C—, $C_{1-4}$-alkyl-NH—(O)C—, $C_{1-4}$-alkyl-O—(O)C—, $H_2N$—(HO—N)C—, morpholinyl-(O)C—, $C_{1-4}$-alkyl-$SO_2$— and 4,5-dimethyloxazol-2-yl; preferably NC—;

$R^{1.3}$ is selected from the group consisting of H, $C_{1-4}$-alkyl-, $C_{1-4}$-alkyl-O— and benzyl-; preferably H or $C_{1-4}$-alkyl-;

or two $R^{1.3}$ are together $C_{2-5}$-alkylene forming a carbocyclic heteroring;

$R^{1.4}$ is $C_{1-4}$-alkyl-;

$R^{1.5}$ is selected from the group consisting of H, NC—, $C_{1-4}$-alkyl- and $C_{1-4}$-alkyl-O—$C_{1-4}$-alkyl-;

x is 0 or 1; preferably 1;

$R^2$ is

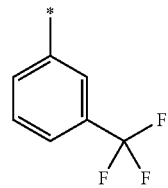 [SMILES: *c1cccc(C(F)(F)F)c1]

$R^3$ is $C_{1-4}$-alkyl- or 4-cyanophenyl;
Y is CH or N;
or a pharmaceutically acceptable salt thereof.

Preferred are the above compounds of formula 1, wherein
A is phenyl;
$R^1$ is selected from the group consisting of

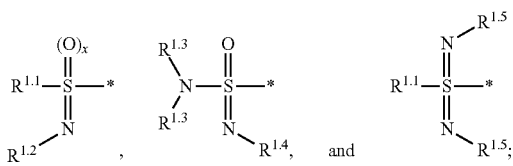

$R^{1.1}$ is methyl;
$R^{1.2}$ is selected from the group consisting of H, NC—, $O_2N$—, methyl, $CH_3$—(O)C—, $H_2N$—(O)C—, $CH_3$—NH—(O)C—, $CH_3$—O—(O)C—, $H_2N$—(HO—N)C—, morpholinyl-(O)C—, $CH_3$—$SO_2$— and 4,5-dimethyloxazol-2-yl;

$R^{1.3}$ is selected from the group consisting of H, methyl, $CH_3$—O— and benzyl-; or two $R^{1.3}$ are together —$(CH_2)_5$—;

$R^{1.4}$ is methyl;
$R^{1.5}$ is selected from the group consisting of H, NC—, methyl and $CH_3$—O—$(CH_2)_2$—;

x is 0 or 1;
$R^2$ is

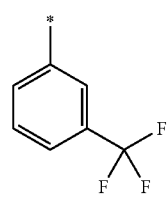 [SMILES: *c1cccc(C(F)(F)F)c1]

$R^3$ is methyl- or 4-cyanophenyl;
Y is CH or N;
or a pharmaceutically acceptable salt thereof.

Preferred are the above compounds of formula 1, wherein
A is phenyl;
$R^1$ is selected from the group consisting of formulas (a) to (w):

(a)
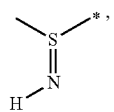

-continued (u)
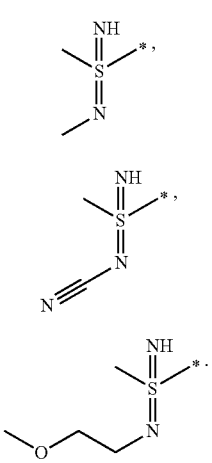

(v)

(w)

$R^2$ is

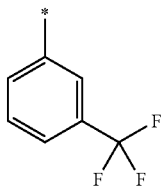

$R^3$ is methyl- or 4-cyanophenyl;

Y is CH or N;

or a pharmaceutically acceptable salt thereof.

Preferred are the compounds of formula (1A)

(1A)
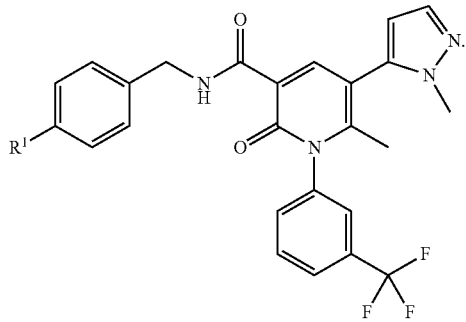

Any and each of the above definitions A, Y, x, $R^1$, $R^2$ and $R^3$ may be combined with each other.

In some of the embodiments of the present invention, the residue $R^1$ is chiral, preferred is the eutomer.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk "*", a dashed or a dotted line may be used in sub-formulas to indicate the bond which is connected to the core molecule as defined.

For example, the term "3-carboxypropyl-group" represents the following substituent:

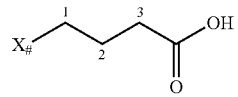

wherein the carboxy group is attached to the third carbon atom of the propyl group. The terms "1-methylpropyl-", "2,2-dimethylpropyl-" or "cyclopropylmethyl-" group represent the following groups:

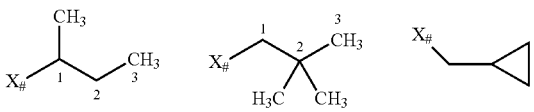

A X with a subscript number or "#", a dashed or a dotted line may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, i.e. more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidinyl, sodium hydroxide, triethanolamine (2,2',2''-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term room temperature denotes a temperature of about 20° C., e.g. 15 to 25° C. as a rule.

The term "$C_{1-n}$-alkyl", wherein n is an integer from 2 to 6, either alone or in combination with another radical denotes an acyclic, saturated, branched or linear hydrocarbon radical with 1 to 6 C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-6}$-alkylene" wherein n is an integer 2 to 6, either alone or in combination with another radical, denotes an acyclic, straight or branched chain divalent alkyl radical containing from 1 to 6 carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

The term "$C_{2-n}$-alkylene" wherein n is an integer 3 to 5, either alone or in combination with another radical, denotes an acyclic, straight or branched chain divalent alkyl radical containing from 2 to 5 carbon atoms. For example the term $C_{2-5}$-alkylene includes —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

By the term "halo" added to a "alkyl", "alkylene" or "cycloalkyl" group (saturated or unsaturated) is such a alkyl or cycloalkyl group meant wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

The term "$C_{3-6}$-cycloalkyl", wherein n is an integer from 4 to 6, either alone or in combination with another radical denotes a cyclic, saturated, unbranched hydrocarbon radical with 3 to 6 C atoms. For example the term $C_{3-6}$-cycloalkyl includes cyclopropyl, cyclobutyl, cyclopentyl and cyclohexyl.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

With the elements of a ring the atoms forming this ring are meant. So, a phenyl ring contains 6 elements which are all carbon atoms, a pyrrol ring contains 5 elements, wherein 4 elements are carbon atoms and the remaining element is a nitrogen atom.

The term "aromatic heteroring" means a unsaturated monocyclic-ring system containing one, two, three or four heteroatoms selected from N, (O$^-$)N$^+$, O or (O)$_r$S, wherein r=0, 1 or 2, consisting of four, five or six ring atoms. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

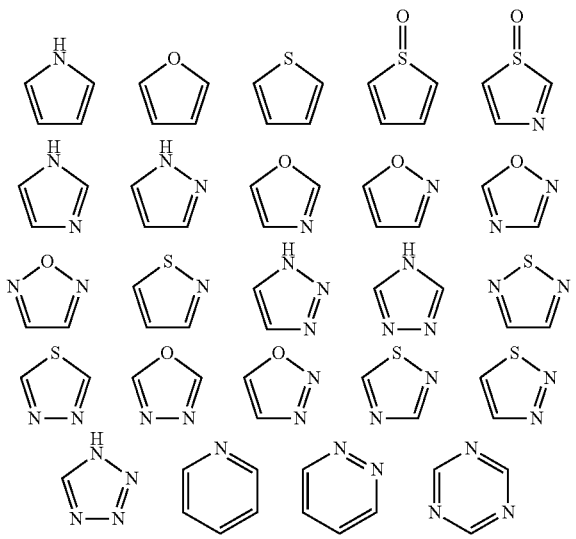

PREPARATION

General Synthetic Methods

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes.

Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Compounds of the invention V are accessible using the synthetic route illustrated in Scheme 1; $R^1$ having the meaning as defined hereinbefore and hereinafter.

SCHEME 1

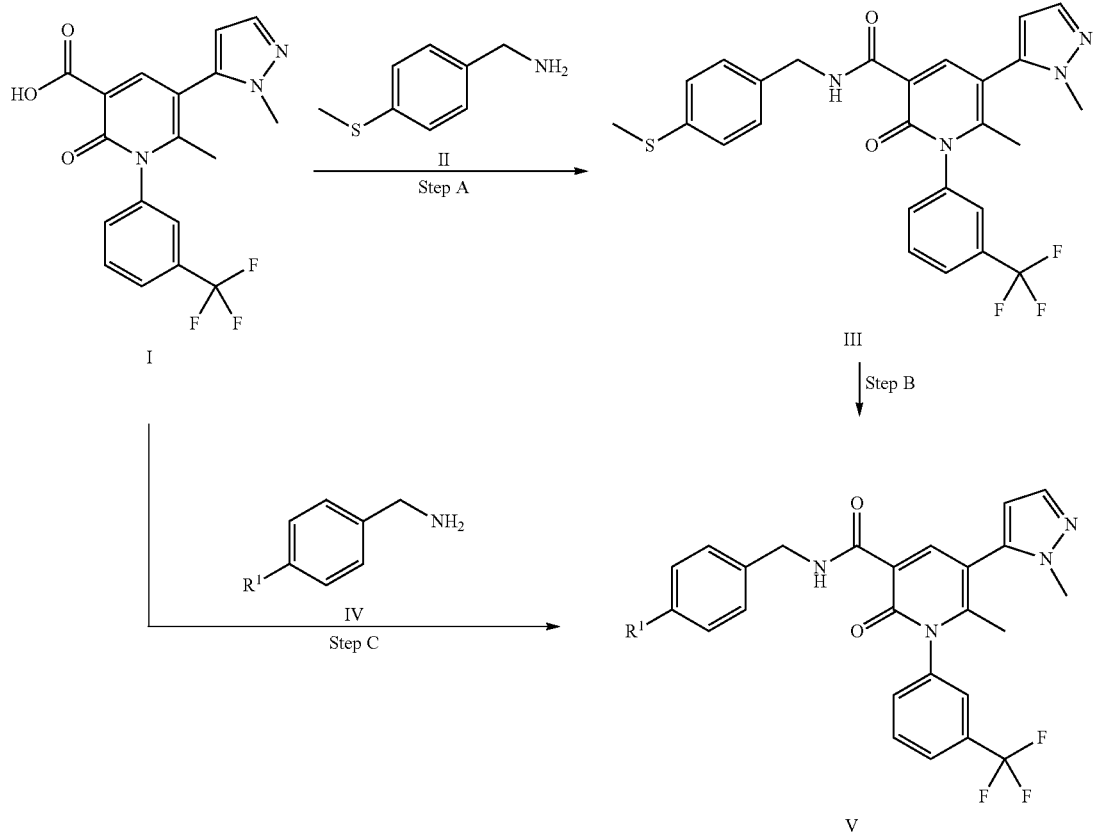

The synthesis of starting material I has been described in WO10094964.

The amide coupling (Step A, starting material I→intermediates III; Step C, starting material I→compounds of the invention V) can be achieved by reacting carboxylic acid starting material I with substituted benzylamines II or IV in the presence of an amide coupling reagent, for example O-(benzotriazol-1-yl)-N,N,N',N'-tetramethyluronium hexafluorophosphate (HBTU), O-(benzotriazol-1-yl)-N,N, N',N'-tetramethyluronium tetrafluoroborate (TBTU) or propane phosphonic acid anhydride, and in the presence of a base, for example triethylamine, diisopropylethylamine (DIPEA, Hünig's base) or N-methyl-morpholine, in an organic solvent, for example N,N-dimethylformamide (DMF), N-methyl-2-pyrrolidone (NMP) or dimethylacetamide (DMA) or mixtures thereof. The reaction usually takes place within 1 to 72 hours. Preferred reaction temperatures are between 0° C. and 50° C., most preferred room temperature. Alternatively, the carboxylic acid intermediates can be activated first as described in US2003/87940, for example with 1,1'-carbonyldiimidazole (CDI) in DMF, followed by reaction with the amine II or IV.

An alternative synthetic route for the preparation of compounds of the invention V by derivatization of intermediate III (step B, intermediates III→compounds of the invention V) is described in the following paragraphs and scheme 2, scheme 3 and scheme 4.

The synthesis of sulfinimides (sulfilimines) and sulfonimides (sulfoximines) has been extensively described in Reggelin et al. (*Synthesis*, 2000, 1-64) and Bolm et al. (*Chem. Lett.* 2004, 33, 482-487). The general processes for the preparation of N-cyano-sulfonimides (N-cyanosulfoximines, intermediates VIII) are illustrated in scheme 2. As indicated, the order of imination and oxidation can usually be interchanged, and the syntheses can likewise start from sulfoxides instead of sulfides.

Intermediates VII can be prepared as described in Bolm et al. (*Org. Lett.* 2007, 9, 3809-3811) via direct imination of a thioether (intermediates VI) with cyanamide (Step D, intermediates VI→intermediates VII) by reaction with an halogenating agent, for example N-bromo- or N-chlorosuccinimide, tert-butyl hypochlorite or iodine in the presence of cyanamide and a base, for example potassium or sodium tert-butoxide, in an organic solvent, for example methanol, tetrahydrofuran (THF) or acetonitrile. The reaction usually takes place within 1 to 72 hours. Preferred reaction temperatures are between 0° C. and 50° C., most preferred is room temperature. Alternatively, the imination (Step D, intermediates VI→intermediates VII) can be achieved as described in Bolm et al. (*Org. Lett.* 2007, 9, 2951-2954), by using phenyliodo diacetate [PhI(OAc)$_2$] and cyanamide in an organic solvent, for example acetonitrile or tetrahydrofuran (THF). The reaction usually takes place within 1 to 72 hours. Preferred reaction temperatures are between 0° C. and room temperature.

The oxidation (Step E, intermediates VII→intermediates VIII, intermediates X→intermediates XI) can be achieved using a peroxycarboxylic acid as oxidizing agent, for example meta-chloroperoxybenzoic acid (mCPBA), optionally in the presence of a base, for example potassium carbonate, in an organic solvent, for example ethanol, methanol, dichloromethane or chloroform. The reaction usually takes place within 1 to 72 hours. Preferred reaction temperatures are between 0° C. and room temperature. Alternatively, other common oxidizing agents may be used to achieve this transformation, for example hydrogen peroxide, tert-butyl hydroperoxide, sodium hypochlorite, sodium iodate, sodium periodate, potassium permanganate, ruthenium tetroxide, potassium peroxymonosulfate (Oxone) or dimethyldioxirane.

Intermediates IX can be obtained by imination of intermediates VI (Step F, intermediates VI→intermediates IX) as described in Bolm. et al. (*Org. Lett.* 2004, 6, 1305-1307, by reacting a thioether (intermediates VI) with trifluoroacetamide, phenyliodo diacetate [PhI(OAc)$_2$], rhodium acetate dimer [Rh$_2$(OAc)$_4$] and MgO in an organic solvent, for example dichloromethane. The reaction usually takes place within 1 to 72 hours. Preferred reaction temperatures are between 0° C. and room temperature.

SCHEME 2

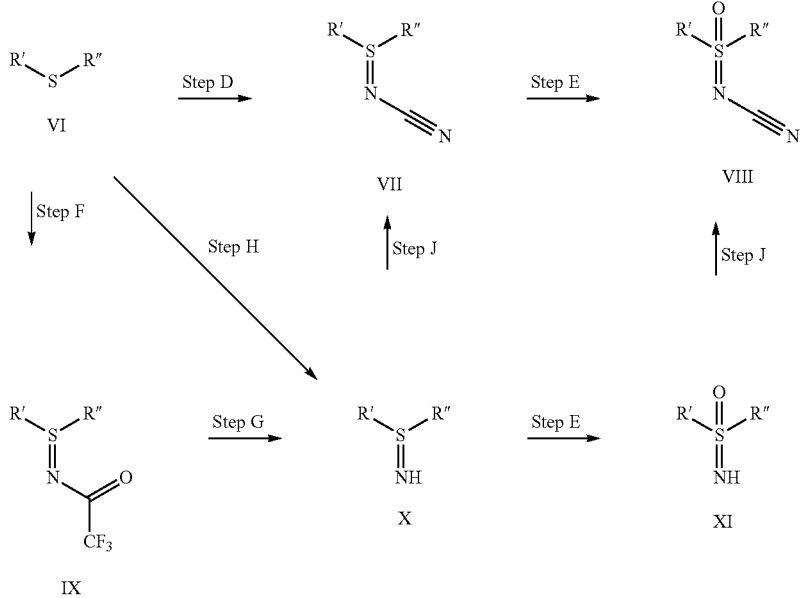

The cleavage of the trifluoroacetamide (Step G, intermediates IX→intermediates X) can be achieved as described in Bolm. et al. (*Org. Lett.* 2004, 6, 1305-1307), using a base, for example potassium carbonate, in an organic solvent, for example methanol. The reaction usually takes place within 1 to 72 hours. Preferred reaction temperatures are between 0° C. and 50° C., most preferred room temperature.

Alternatively, intermediates X can be prepared by the imination of intermediates VI (step H, intermediates VI→intermediates X) using other electrophilic nitrogen sources, for example tert-butyl 3-(4-cyano-phenyl)-oxaziridine-2-carboxylate (followed by cleavage of the Boc-protecting group), O-mesityl sulfonyl hydroxylamine (MSH), or hydrazoic azid.

The cyanation of sulfinimides or sulfonimides (Step J, intermediates X→intermediates VII, intermediates XI→intermediates VIII) can be achieved as described in Bolm et al. (*Org. Lett.* 2007, 9, 2951-2954), by reacting the starting material with cyanogen bromide, optionally 4-dimethylaminopyridine (DMAP) and optionally a base, for example triethylamine, in an organic solvent, for example dichloromethane. The reaction usually takes place within 1 to 72 hours. Preferred reaction temperatures are between 0° C. and 50° C., most preferred room temperature.

The synthesis of sulfonimidamides has been described in Johnson et al. (*J. Org. Chem.* 1975, 44, 2055-2061), Bolm et al. (*J. Org. Chem.* 2010, 75, 3301-3310) and in WO09156336. The general synthetic scheme for the preparation of sulfonimidamides XV from sulfinamides XII is depicted in the following scheme 3.

SCHEME 3

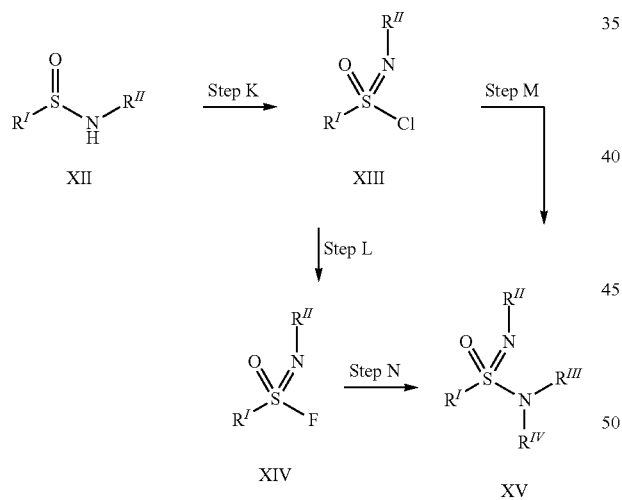

Sulfinamides (starting material XII) can be prepared as described in Johnson et al. (*J. Org. Chem.* 1975, 44, 2055-2061) by reacting sulfinyl chlorides with a primary or secondary amine, optionally in the presence of an additional base, for example pyridine or a tertiary amine, in an organic solvent, for example dichloromethane, tetrahydrofuran, diethylether, acetonitrile, toluene, N,N-dimethylformamide, ethanol or ethyl acetate. The reaction usually takes place within 1-72 hours. Preferred reaction temperatures are between 0° C. and room temperature.

Sulfonimidoyl chlorides (intermediates XIII) can be prepared as described in Johnson et al. (*J. Org. Chem.* 1975, 44, 2055-2061), by reacting sulfinamides (starting material XII) with a chlorinating agent, for example chlorine, N-chlorosuccinimide (NCS), N-chlorobenzotriazole or tert-butyl hypochlorite in an organic solvent, for example dichloromethane, diethylether, benzene, toluene, carbon tetrachloride, acetonitrile or tetrahydrofuran (Step K). The reaction usually takes place within less than 1 hour. Preferred reaction temperatures are between −78° C. and room temperature, mostly preferred between 0° C. and room temperature.

Sulfonimidoyl fluorides (intermediates XIV) can be prepared as described in Johnson et al. (*J. Org. Chem.* 1983, 48, 1-3) and Gnamm et al. (*Bioorg. Med. Chem. Lett.* 2012, 22, 3800-3806), by reacting sulfonimidoyl chlorides (intermediates XIII) with a fluoride salt, for example potassium fluoride, sodium fluoride or tetrabutylammonium fluoride, optionally in the presence of a crown ether, for example 18-crown-6, in an organic solvent, for example acetonitrile or tetrahydrofuran (Step L). The reaction takes place within 1 to 24 hours. Preferred reaction temperatures are between 0° C. and room temperature, mostly preferred room temperature.

Sulfonimidamides (intermediates XV) can be prepared as described in Johnson et al. (*J. Org. Chem.* 1975, 44, 2055-2061), Bolm et al. (*J. Org. Chem.* 2010, 75, 3301-3310) and WO09156336 by reacting sulfonimidoyl chlorides (intermediates XIII) with a primary or secondary, aliphatic or aromatic amine, optionally in the presence of an additional base, for example pyridine or a tertiary amine, in an organic solvent, for example acetonitrile, tetrahydrofuran, N,N-dimethylformamide or benzene (Step M). The reaction takes place within 1 to 72 hours. Preferred reaction temperatures are between 0° C. and room temperature.

Alternatively, sulfonimidamides (intermediates XV) can be prepared as described in Gnamm et al. (*Bioorg. Med. Chem. Lett.* 2012, 22, 3800-3806) by reacting sulfonimidoyl fluorides (intermediates XIV) with a primary or secondary, aliphatic or aromatic amine, optionally in the presence of an additional base, for example pyridine or a tertiary amine, for example 1,8-diazabicyclo[5.4.0]undec-7-ene (DBU), in an organic solvent, for example acetonitrile, tetrahydrofuran, N,N-dimethylformamide or benzene (Step N). The reaction takes place within 1 to 72 hours. Preferred reaction temperatures are between 0° C. and the boiling point of the solvent, mostly preferred between room temperature and 110° C.

The synthesis of sulfondiimines has been described in Appel et al. (*Chem. Ber.* 1966, 99, 3108-3117), Laughlin et al. (*J. Am. Chem. Soc.* 1967, 89, 2435-2443), Haake (*Tetrahedron Lett.* 1970, 11, 4449-4450) and Bolm et al. (*Angew. Chem. Int. Ed.* 2012, 51, 4440-4443) and is illustrated in Scheme 4.

SCHEME 4

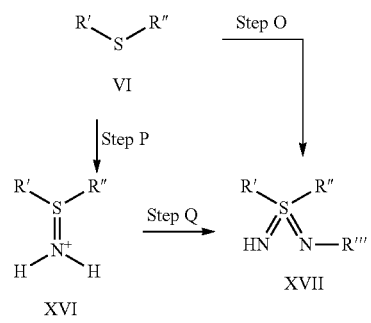

Sulfondiimides XVII can be prepared as described by Haake (*Top. Sulfur Chem.* 1976, 1, 185-215) and Ried et al.

(*Chem. Ber.* 1984, 117, 2779-2784) in one step from sulfides VI (Step O, intermediates VI→intermediates XVII) by reacting the latter with liquid ammonia in the presence of tert-butyl hypochlorite in a suitable organic solvent, for example acetonitrile. Alternatively, as described by Haake (*Tetrahedron Lett.* 1970, 11, 4449-4450), chloramine-T or N-chlorosuccinimide can be used as chlorite source. The reaction takes place within 1 to 72 hours. Preferred reaction temperatures are between −60° C. and room temperature, mostly preferred between −60° C. and −40° C.

Alternatively, following a two-step procedure described by Bolm et al. (*Angew. Chem. Int. Ed.* 2012, 51, 4440-4443), sulfondiimides XVII can be prepared via the corresponding sulfiliminium salts XVI (Step P, intermediates VI→intermediates XVI, Step Q, intermediates XVI→intermediates XVII).

Sulfiliminium salts XVI can be prepared as described in Haake et al. (*Synthesis* 1983, 919) by reacting sulfides VI with O-mesitylsulfonyl hydroxylamine in an organic solvent, for example dichloromethane. The reaction takes place within 1 to 72 hours. Preferred reaction temperatures are between 0° C. and room temperature, mostly preferred room temperature.

Sulfondiimides XVII can be prepared by reacting sulfiliminium salts XVI with ammonia or an aliphatic or aromatic amine in the presence of an oxidizing agent, such as N-chlorosuccinimide, or with chloramine-T, in an organic solvent, for example dichloromethane or N,N-dimethylformamide, optionally in the presence of an additional base, for example a tertiary amine, for example N,N-diisopropylethylamine or triethylamine. The reaction takes place within 1 to 72 hours. Preferred reaction temperatures are between 0° C. and room temperature, mostly preferred room temperature.

Compounds of the invention XX are accessible using the synthetic route illustrated in Scheme 5; $R^1$, $R^2$ and $R^3$ having the meaning as defined hereinbefore and hereinafter.

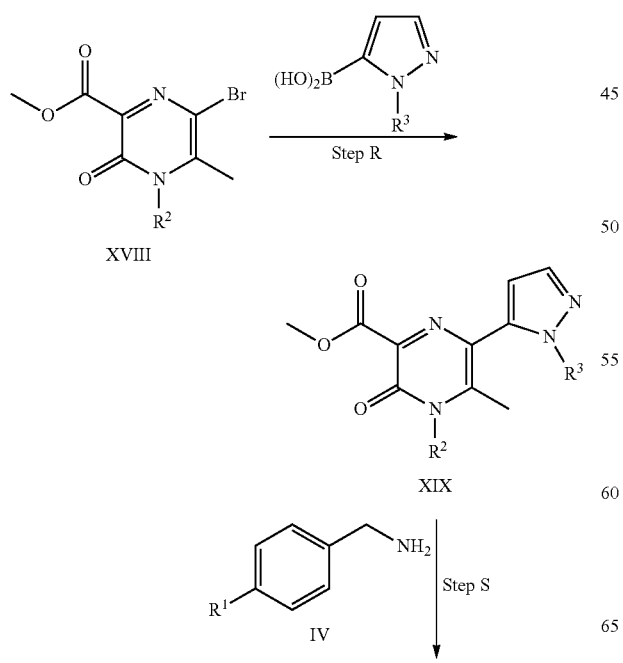

Starting material XVIII can be prepared as described in WO09061271.

Intermediates XIX (Step R, starting materials XVIII→intermediates XIX) can be prepared as described in WO11110852, by reacting starting materials XVIII with aryl or heteroaryl boronic acids or the corresponding boronic esters in the presence of a palladium catalyst, for example tetrakis(triphenylphosphine)palladium(0) or [1,1'-bis(diphenyl-phosphino) ferrocene]dichloropalladium(II), and in the presence of a base, for example, potassium carbonate, barium dihydroxide or cesium carbonate, in an organic solvent, for example toluene, benzene, ethanol, ethylene glycol dimethyl ether, acetonitrile, 1,4-dioxane or mixtures thereof, optionally in the presence of water. The reaction usually takes place within 1 to 72 hours. Preferred reaction temperatures are between 50° C. and 150° C.

Compounds of the invention XX can be prepared as described in WO11110852, by reacting intermediates XIX with an amine IV in an organic solvent, for example tetrahydrofuran, acetonitrile or N,N-dimethylformamide. The reaction usually takes place within 1 to 72 hours. Preferred reaction temperatures are between room temperature and the boiling point of the solvent, most preferred between room temperature and 50° C.

SYNTHETIC EXAMPLES $^1$H NMR spectra and/or mass spectra have been obtained of the compounds prepared. Compounds given with a specific configuration at a stereocenter are isolated as pure isomers.

Enantiomerically pure compounds with unknown absolute configuration are marked with an asterix (*) as exemplified in the following structure (confer example 16):

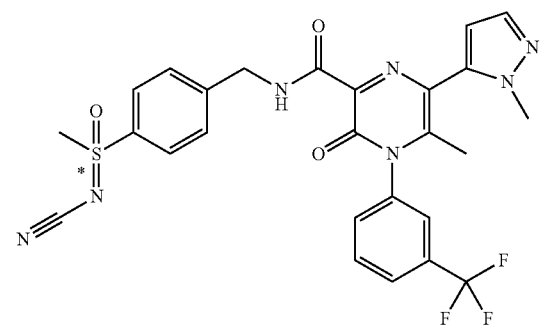 [SMILES: Cc1c(-c2ccnn2C)nc(C(=O)NCc2ccc(S(C)(=O)=NC#N)cc2)c(=O)n1-c1cccc(C(F)(F)F)c1]

The following are representative compounds of the invention which can be made by the general synthetic schemes, the examples, and known methods in the art.

The retention times given for the compounds below are measured under the following conditions (TFA: trifluoroacetic acid, DEA: diethylamine, scCO$_2$: supercritical carbon dioxide):

| Method name: | 003_CA04 |
| --- | --- |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 98 | 2 | 2.0 | 60.0 |
| 1.2 | 0 | 100 | 2.0 | 60.0 |
| 1.4 | 0 | 100 | 2.0 | 60.0 |

| Method name: | V001_007 |
| --- | --- |
| Column: | XBridge C18, 4.6 × 30 mm, 3.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

| Method name: | V003_003 |
| --- | --- |
| Column: | XBridge C18, 4.6 × 30 mm, 3.5 μM |
| Column Supplier: | Waters |

| Gradient/ Solvent Time [min] | % Solvent [H₂O, 0.1% NH₃] | % Solvent [acetonitrile] | Flow [ml/min] | Temperature [° C.] |
| --- | --- | --- | --- | --- |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

| Method name: | V011_S01 |
| --- | --- |
| Column: | XBridge C18, 4.6 × 30 mm, 3.5 μm |
| Column Supplier: | Waters |

| Gradient/ Solvent Time [min] | % Solvent [H₂O, 0.1% NH₃] | % Solvent [acetonitrile] | Flow [ml/min] | Temperature [° C.] |
| --- | --- | --- | --- | --- |
| 0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method name: | V012_S01 |
| --- | --- |
| Column: | XBridge C18, 4.6 × 30 mm, 3.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method name: | X001_004 |
| --- | --- |
| Column: | XBridge C18, 2.1 × 20 mm, 2.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0 | 95 | 5 | 1.4 | 60 |
| 0.05 | 95 | 5 | 1.4 | 60 |
| 1 | 0 | 100 | 1.4 | 60 |
| 1.1 | 0 | 100 | 1.4 | 60 |

-continued

| Method name: | X012_S01 |
| --- | --- |
| Column: | XBridge BEH C18, 2.1 × 30 mm, 1.7 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Method name: | Z002_006 |
| --- | --- |
| Column: | Sunfire C18, 3 × mm,, 2.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method name: | Z003_004 |
| --- | --- |
| Column: | XBridge C18, 3 × 30 mm, 2.5 μm |
| Column Supplier: | Waters |

| Gradient/ Solvent Time [min] | % Solvent [H₂O, 0.1% NH₃] | % Solvent [methanol] | Flow [ml/min] | Temperature [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method name: | Z009_001 |
| --- | --- |
| Column: | XBridge Phenyl, 3 × 30 mm, 2.5 μm |
| Column Supplier: | Waters |

| Gradient/ Solvent Time [min] | % Solvent [H₂O, 0.1% NH₃] | % Solvent [methanol] | Flow [ml/min] | Temperature [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method name: | Z012_S04 |
| --- | --- |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [methanol] | Flow [ml/min] | Temperature [° C.] |
| --- | --- | --- | --- | --- |
| 0.0 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method name: | Z018_S04 |
| --- | --- |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [acetonitrile] | Flow [ml/min] | Temperature [° C.] |
| --- | --- | --- | --- | --- |
| 0.0 | 97 | 3 | 2.2 | 60 |
| 0.20 | 97 | 3 | 2.2 | 60 |

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 1.20 | 0 | 100 | 2.2 | | 60 |
| 1.25 | 0 | 100 | 3 | | 60 |
| 1.40 | 0 | 100 | 3 | | 60 |

| Method name: | I_IC_30_MeOH_DEA |
|---|---|
| Column: | Chiralpak IC 4.6 × 250 mm, 5 µm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

| Method name: | I_IC_40_MeOH_DEA |
|---|---|
| Column: | Chiralpak IC 4.6 × 250 mm, 5 µm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 40 | 60 | 4 | 40 | 150 |

| Method name: | I_IC_50_MeOH_DEA |
|---|---|
| Column: | Chiralpak IC 4.6 × 250 mm, 5 µm |
| Column Supplier: | Daicel |

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 50 | 50 | 4 | 40 | 150 |

Syntheses of Starting Materials

The Following Starting Materials are Prepared as Described in the Literature Cited:
6-Methyl-5-(2-methylpyrazol-3-yl)-2-oxo-1-[3-(trifluoromethyl)phenyl]pyridine-3-carboxylic acid: WO10094964; methyl 6-[2-(4-cyanophenyl)pyrazol-3-yl]-5-methyl-3-oxo-4-[3-(trifluoromethyl)phenyl]pyrazine-2-carboxylate: WO11110852; methyl 6-bromo-5-methyl-3-oxo-4-[3-(trifluoromethyl)phenyl]pyrazine-2-carboxylate: WO09061271; 2-benzylisoindoline-1,3-dione: WO07093452; tert-butyl hypochlorite: *Org. Synth. Coll. Vol.* 1973, 5, 184.

The Synthesis of the Following Starting Materials has been Described Before in the Literature Cited:
2-[(4-Methylsulfanylphenyl)methyl]isoindoline-1,3-dione: WO0216318; O-Mesityl-sulfonylhydroxylamine: WO11130342.

Intermediate 1

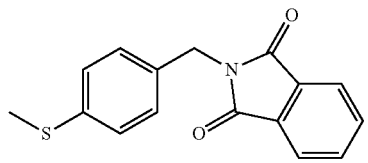 [SMILES: CSc1ccc(CN2C(=O)c3ccccc3C2=O)cc1]

2-[(4-Methylsulfanylphenyl)methyl]isoindoline-1,3-dione

A mixture of (4-methylsulfanylphenyl)methanamine (2.00 mL, 2.20 g, 14.38 mmol) and phthalic anhydride (2.34 g, 15.79 mmol) in acetic acid (40 mL) is heated at reflux for 3 h. The mixture is concentrated under reduced pressure, and the residue is partitioned between water and dichloromethane. The phases are separated, and the aqueous phase is extracted twice with dichloromethane. The combined organic layers are concentrated under reduced pressure and the residue is purified by flash chromatography on silica (gradient cyclohexane/ethyl acetate 9:1 to 7:3). Yield: 3.60 g; ESI mass spectrum: [M+H]$^+$=284; Retention time HPLC: 0.75 min (X001_004).

Intermediate 2

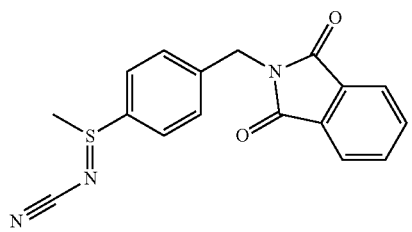 [SMILES: C/S(=N\C#N)c1ccc(CN2C(=O)c3ccccc3C2=O)cc1]

[[4-[(1,3-Dioxoisoindolin-2-yl)methyl]phenyl]-methyl-λ$^4$-sulfanylidene]cyanamide A solution of 2-[(4-methylsulfanylphenyl)methyl]isoindoline-1,3-dione (intermediate 1, 3.60 g, 12.71 mmol), cyanamide (694 mg, 16.52 mmol) and potassium tert-butoxide (1.71 g, 15.25 mmol) in methanol (30 mL) is treated with N-bromosuccinimide (3.39 g, 19.06 mmol). The mixture is stirred for 1 h and concentrated under reduced pressure. Saturated aqueous Na$_2$S$_2$O$_3$ solution is added, and the mixture is extracted twice with dichloromethane. The combined organic layers are dried over Na$_2$SO$_4$ and concentrated under reduced pressure. The residue is purified by flash chromatography on silica (gradient cyclohexane/ethyl acetate 1:1 to ethyl acetate to ethyl acetate/methanol 4:1). Yield: 2.86 g; ESI mass spectrum: [M+H]$^+$=324; Retention time HPLC: 0.52 min (X001_004).

Intermediate 3

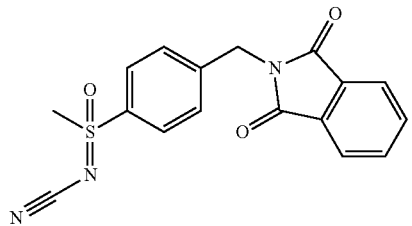 [SMILES: CS(=O)(=NC#N)c1ccc(CN2C(=O)c3ccccc3C2=O)cc1]

[[4-[(1,3-Dioxoisoindolin-2-yl)methyl]phenyl]-methyl-oxo-λ$^6$-sulfanylidene]cyanamide A solution of [[4-[(1,3-dioxoisoindolin-2-yl)methyl]phenyl]-methyl-λ$^4$-sulfanylidene]-cyanamide (intermediate 2, 5.75 g, 17.78 mmol) and potassium carbonate (7.37 g, 53.34 mmol) in ethanol (130 mL) is cooled at 0° C. and treated with meta-chloroperoxybenzoic acid (mCPBA, 77%, 5.98 g, 26.67 mmol). The reaction mixture is warmed at room temperature and stirred overnight. More mCPBA (77%, 2.39 g, 10.66 mmol) is added and the mixture is stirred for 4 h. Saturated aqueous $Na_2S_2O_3$ solution is added, and the mixture is extracted twice with dichloromethane. The combined organic layers are dried over $Na_2SO_4$ and concentrated under reduced pressure. The residue is purified by flash chromatography on silica (gradient cyclohexane/ethyl acetate 1:1 to ethyl acetate). Yield: 2.47 g;

ESI mass spectrum: [M+H]=340; Retention time HPLC: 0.56 min (X001_004).

Intermediates 3A and 3B

Enantiomers of Intermediate 3

The enantiomers of racemic [[4-[(1,3-dioxoisoindolin-2-yl)methyl]phenyl]-methyl-oxo-$\lambda^6$-sulfanylidene]cyanamide (intermediate 3, 2.00 g, 5.90 mmol) are separated by preparative supercritical fluid chromatography on a chiral phase (Daicel Chiralcel OZ-H, 10 mm×250 mm, 5 µm, 32% MeOH+ 0.2% diethylamine in supercritical $CO_2$, 40° C., 120 bar back pressure).

Intermediate 3A

Yield: 600 mg; ESI mass spectrum [M+H]$^+$=340; Retention time: 10.19 min (early eluting enantiomer) (Daicel Chiralpak® IA 4.6 mm×250 mm×5 µm, 1 mL/min, 20 min, 70% hexane+15% isopropanol+15% dichloromethane+0.1% TFA, 20° C.).

Intermediate 3B

Yield: 700 mg; ESI mass spectrum [M+H]$^+$=340; Retention time: 10.70 min (late eluting enantiomer) (Daicel Chiralpak® IA 4.6 mm×250 mm×5 µm, 1 mL/min, 20 min, 70% hexane+15% isopropanol+15% dichloromethane+0.1% TFA, 20° C.).

Intermediate 4

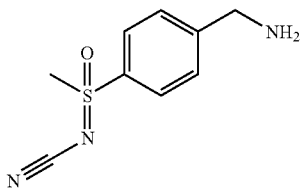

[[4-(Aminomethyl)phenyl]-methyl-oxo-$\lambda^6$-sulfanylidene]cyanamide

A solution of [[4-[(1,3-dioxoisoindolin-2-yl)methyl]phenyl]-methyl-oxo-$\lambda^6$-sulfanylidene]-cyanamide (intermediate 3, 684 mg, 2.02 mmol) and 1,2-diaminoethane (243 µL, 219 mg, 3.64 mmol) in a mixture of acetonitrile (8 mL), tetrahydrofuran (4 mL) and ethanol (4 mL) is heated at 60° C. for 5 h. All volatiles are removed under reduced pressure and the residue is suspended in dichloromethane. The mixture is filtered and the filtrate is concentrated under reduced pressure. Yield: 326 mg; ESI mass spectrum: [M+H]$^+$=210; Retention time HPLC: 0.22 min (V001_007).

Intermediates 4A AND 4B

Enantiomers of Intermediate 4

Intermediate 4A

The early eluting enantiomer of intermediate 4 is prepared in analogy to racemic [[4-(aminomethyl)phenyl]-methyl-oxo-$\lambda^6$-sulfanylidene]cyanamide (intermediate 4), using the early eluting enantiomer of intermediate 3 (intermediate 3A) as starting material. ESI mass spectrum [M+H]$^+$=210; Retention time: 2.92 min (early eluting enantiomer) (I_IC_30_MeOH_DEA).

Intermediate 4B

The late eluting enantiomer of intermediate 4 is prepared in analogy to racemic [[4-(aminomethyl)phenyl]-methyl-oxo-$\lambda^6$-sulfanylidene]cyanamide (intermediate 4), using the late eluting enantiomer of intermediate 3 (intermediate 3B) as starting material. ESI mass spectrum [M+H]$^+$=210; Retention time: 2.92 min (early eluting enantiomer) (I_IC_30_MeOH_DEA).

Intermediate 5

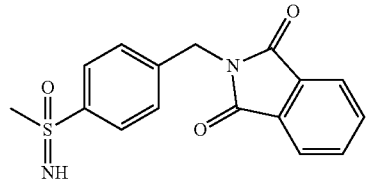 [SMILES: CS(=N)(=O)c1ccc(CN2C(=O)c3ccccc3C2=O)cc1]

2-[[4-(Methylsulfonimidoyl)phenyl]methyl]isoindoline-1,3-dione

Step 1

N-[[4-[(1,3-Dioxoisoindolin-2-yl)methyl]phenyl]-methyl-oxo-$\lambda^6$-sulfanylidene]-2,2,2-trifluoro-acetamide A solution of [[4-[(1,3-dioxoisoindolin-2-yl)methyl]phenyl]-methyl-oxo-$\lambda^6$-sulfanylidene]-cyanamide (intermediate 4, 2.00 g, 5.90 mmol) in dichloromethane (20 mL) is cooled at 0° C. and treated with trifluoroacetic anhydride (2.5 mL, 3.73 g, 17.7 mmol). The mixture is stirred at 0° C. for 2 h and warmed at room temperature. Water is added and the phases are separated. The aqueous layer is extracted three times with dichloromethane, and the combined organic layers are dried over $Na_2SO_4$ and concentrated under reduced pressure. The residue is purified by flash chromatography on silica (ethyl acetate/dichloromethane 9:1). Yield: 2.10 g.

Step 2

2-[[4-(Methylsulfonimidoyl)phenyl]methyl]isoindoline-1,3-dione

Potassium carbonate (3.37 g, 24.4 mmol) is added to a solution of N-[[4-[(1,3-dioxoisoindolin-2-yl)methyl]phenyl]-methyl-oxo-$\lambda^6$-sulfanylidene]-2,2,2-trifluoro-acetamide (Step 1, 2.00 g, 4.88 mmol) in methanol, and the mixture

Intermediate 6

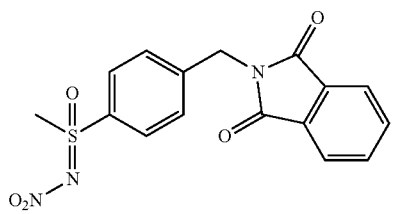 [SMILES: CS(=O)(=N[N+](=O)[O-])c1ccc(CN2C(=O)c3ccccc3C2=O)cc1]

N-[[4-[(1,3-Dioxoisoindolin-2-yl)methyl]phenyl]-methyl-oxo-$\lambda^6$-sulfanylidene]-nitramide A solution of 2-[[4-(methylsulfonimidoyl)phenyl]methyl]isoindoline-1,3-dione (intermediate 5, 100 mg, 318 μmol) in dichloromethane (2.0 mL) is cooled at 0° C. and treated with fuming nitric acid (90%, 15 μL, 0.32 mmol). Acetic anhydride (500 μL, 540 mg, 5.29 mmol) and concentrated sulfuric acid (6 μL, 0.1 mmol) is added, and the mixture is stirred at 0° C. for 1 h. The mixture is warmed at room temperature and stirred over night. All volatiles are removed under reduced pressure, and the residue is treated with ethyl acetate and saturated aqueous sodium hydrogen carbonate solution. The phases are separated, and the organic layer is concentrated under reduced pressure. The residue is treated with a mixture of methanol and water, and the precipitate is filtered and dried. Yield: 15 mg; ESI mass spectrum [M+H]$^+$=360, Retention time HPLC: 0.50 min (X012_S01).

Intermediate 7

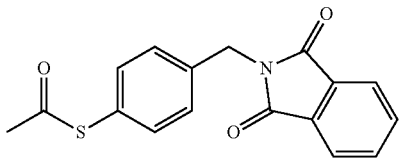 [SMILES: CC(=O)Sc1ccc(CN2C(=O)c3ccccc3C2=O)cc1]

S-[4-[(1,3-Dioxoisoindolin-2-yl)methyl]phenyl] ethanethioate

Step 1

4-[(1,3-Dioxoisoindolin-2-yl)methyl]benzenesulfonyl chloride

Chlorosulfonic acid (12.3 mL, 21.5 g, 186 mmol) is added dropwise at 0° C. to a solution of 2-benzylisoindoline-1,3-dione (22.0 g, 92.7 mmol) in dichloromethane (150 mL), and the mixture is warmed at room temperature and stirred for 1.5 h. The mixture is cooled at 0° C. in an ice bath, treated with thionyl chloride (10.1 mL, 16.6 g, 139 mmol) and heated at reflux for 3.5 h. Another portion of chlorosulfonic acid (3.1 mL, 5.43 g, 46.8 mmol) and thionyl chloride (2.0 mL, 3.28 g, 28.3 mmol) is added, and the mixture is heated at reflux for 1 h. The mixture is stirred at room temperature over night and poured into ice water. The mixture is extracted twice with dichloromethane, and the combined organic layers are concentrated under reduced pressure. Yield: 30.2 g; ESI mass spectrum [M+H]$^+$=336, Retention time HPLC: 1.40 min (V001_007).

Step 2

S-[4-[(1,3-Dioxoisoindolin-2-yl)methyl]phenyl] ethanethioate

A solution of 4-[(1,3-dioxoisoindolin-2-yl)methyl]benzenesulfonyl chloride (step 1, 30.2 g, 90.1 mmol) in toluene (250 mL) is cooled in an ice bath at 0° C. and treated dropwise with a solution of triphenylphosphine (70.9 g, 270.2 mmol) in toluene (250 mL). The mixture is warmed at room temperature and stirred for 2.5 h. Water is added and the phases are separated. The organic layer is concentrated under reduced pressure, and the residue is dissolved in N,N-dimethylformamide (200 mL). Acetic anhydride (29.0 mL, 32.3 g, 307 mmol) is added, and the mixture is stirred at room temperature for 2 h and concentrated under reduced pressure. The residue is purified by flash chromatography on silica (gradient cyclohexane to cyclohexane/ethyl acetate 4:1). Yield: 14.0 g; ESI mass spectrum [M+H]$^+$=312, Retention time HPLC: 1.36 min (V001_007).

Intermediate 8

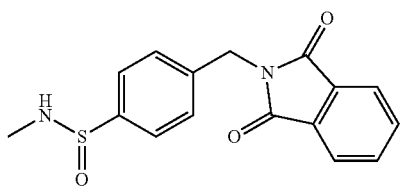 [SMILES: CNS(=O)c1ccc(CN2C(=O)c3ccccc3C2=O)cc1]

4-[(1,3-Dioxoisoindolin-2-yl)methyl]-N-methyl-benzenesulfinamide

A solution of acetic anhydride (4.34 mL, 4.68 g, 45.9 mmol) in dichloromethane (50 mL) is added dropwise to a precooled solution of S-[4-[(1,3-dioxoisoindolin-2-yl)methyl]phenyl]ethanethioate (intermediate 7, 13.0 g, 41.8 mmol) in dichloromethane (500 mL) at −20° C. A solution of sulfuryl chloride (7.42 mL, 12.4 g, 91.8 mmol) in dichloromethane (50 mL) is added, and the mixture is warmed to room temperature. All volatiles are removed under reduced pressure, and the residue is dissolved in dichloromethane (400 mL). The mixture is cooled at 0° C. and treated with methylamine (2.0 M in tetrahydrofuran, 80 mL, 160 mmol). The mixture is warmed at room temperature and stirred for 2 h. Water is added, and the phases are separated. The aqueous layer is extracted twice with dichloromethane, and the combined organic layers are dried over Na$_2$SO$_4$ and concentrated under reduced pressure.

The residue is purified by flash chromatography on silica (ethyl acetate). Yield: 3.44 g; ESI mass spectrum [M+H]⁺=315, Retention time HPLC: 0.89 min (X012_S01).

Intermediate 9

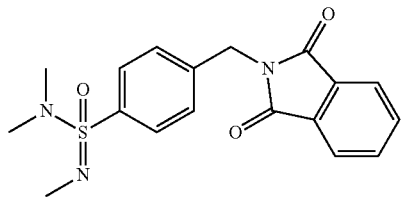 [SMILES: CN=S(=O)(c1ccc(CN2C(=O)c3ccccc3C2=O)cc1)N(C)C]

2-[[4-[S-(Dimethylamino)-N-methyl-sulfonimidoyl]phenyl]methyl]isoindoline-1,3-dione Tert-butyl hypochlorite (60 μL, 58 mg, 0.53 mmol) is added at 0° C. to a mixture of 4-[(1,3-dioxoisoindolin-2-yl)methyl]-N-methyl-benzenesulfinamide (intermediate 8, 150 mg, 0.48 mmol) in acetonitrile (3.0 mL), and the mixture is stirred for 15 min. Dimethylamine (2.0 M in tetrahydrofuran, 360 μL, 0.72 mmol) is added, and the mixture is warmed at room temperature and stirred for 30 min. Water is added, and the mixture is extracted twice with dichloromethane. The combined organic layers are dried over Na₂SO₄ and concentrated under reduced pressure, and the residue is purified by flash chromatography on silica (gradient cyclohexane/ethyl acetate 7:3 to ethyl acetate). Yield: 52 mg; ESI mass spectrum [M+H]⁺=358, Retention time HPLC: 0.43 min (X012_S01).

Intermediate 10

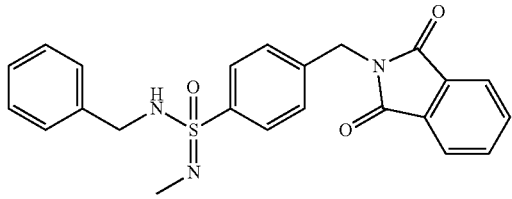 [SMILES: CN=S(=O)(NCc1ccccc1)c1ccc(CN2C(=O)c3ccccc3C2=O)cc1]

2-[[4-[S-(Benzylamino)-N-methyl-sulfonimidoyl]phenyl]methyl]isoindoline-1,3-dione Tert-butyl hypochlorite (40 μL, 38 mg, 0.35 mmol) is added to a mixture of 4-[(1,3-dioxoisoindolin-2-yl)methyl]-N-methyl-benzenesulfinamide (intermediate 8, 93 mg, 0.30 mmol) in tetrahydrofuran (2.0 mL), and the mixture is stirred for 5 min. Benzylamine (76 μL, 75 mg, 0.70 mmol) is added, and the mixture is stirred for 5 min. Water is added, and the mixture is extracted twice with dichloromethane. The combined organic layers are dried over Na₂SO₄ and concentrated under reduced pressure, and the residue is purified by reversed phase HPLC (Waters Xbridge™-C₁₈, gradient of methanol in water, 0.1% NH₃). Yield: 50 mg; ESI mass spectrum [M+H]⁺=420, Retention time HPLC: 1.29 min (Z009_001).

Intermediate 11

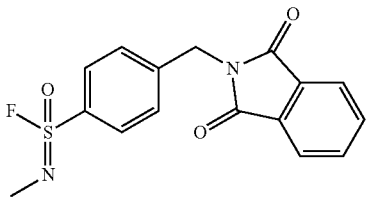 [SMILES: CN=S(=O)(F)c1ccc(CN2C(=O)c3ccccc3C2=O)cc1]

2-[[4-(S-Fluoro-N-methyl-sulfonimidoyl)phenyl]methyl]isoindoline-1,3-dione

Under an atmosphere of argon, 4-[(1,3-dioxoisoindolin-2-yl)methyl]-N-methyl-benzenesulfinamide (intermediate 8, 3.00 g, 9.54 mmol) is dissolved in acetonitrile (100 mL), and the mixture is cooled at 0° C. Tert-butyl hypochlorite (1.18 mL, 1.13 g, 10.5 mmol) is added, and the mixture is stirred at 0° C. for 5 min. Potassium fluoride (2.22 g, 38.2 mmol) and 18-crown-6 (3.78 g, 14.3 mmol) is added, and the mixture is warmed at room temperature. After 30 min, all volatiles are removed under reduced pressure, and the residue is purified by flash chromatography on silica (cyclohexane/ethyl acetate 1:1). Yield: 2.46 g; ESI mass spectrum [M+H]⁺=333, Retention time HPLC: 0.63 min (X012_S01).

Intermediate 12

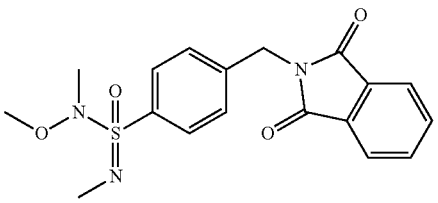 [SMILES: CN=S(=O)(c1ccc(CN2C(=O)c3ccccc3C2=O)cc1)N(C)OC]

2-[[4-[S-[Methoxy(methyl)amino]-N-methyl-sulfonimidoyl]phenyl]methyl]isoindoline-1,3-dione A mixture of N,O-dimethylhydroxylamine hydrochloride (350 mg, 3.59 mmol) and N,N-dimethylformamide (3.0 mL) is treated with 1,8-diazabicyclo[5.4.0]undec-7-en (360 μL, 352 mg, 2.32 mmol) and stirred at room temperature for 5 min. 2-[[4-(S-Fluoro-N-methyl-sulfonimidoyl)phenyl]methyl]isoindoline-1,3-dione (intermediate 11, 215 mg, 0.65 mmol) and N,N-dimethylformamide (2.0 mL) is added, and the mixture is heated at 120° C. for 2 h and cooled at room temperature. Water is added, and the mixture is extracted twice with ethyl acetate. The combined organic layers are concentrated under reduced pressure, and the residue is purified by reversed phase HPLC (Waters Xbridge™-C₁₈, gradient of acetonitrile in water, 0.1% NH₃). Yield: 27 mg; ESI mass spectrum [M+H]⁺=374, Retention time HPLC: 1.19 min (Z003_004).

Intermediate 13

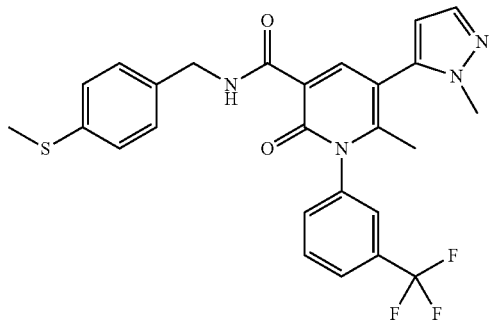 [SMILES: CSc1ccc(CNC(=O)c2cc(-c3ccnn3C)c(C)n(-c3cccc(C(F)(F)F)c3)c2=O)cc1]

6-Methyl-5-(2-methylpyrazol-3-yl)-N-[(4-methylsulfanylphenyl)methyl]-2-oxo-1-[3-(trifluoromethyl)phenyl]pyridine-3-carboxamide N,N-Diisopropylethylamine (900 µL, 5.30 mmol) and N,N,N',N'-tetramethyl-O-(benzotriazol-1-yl)uronium tetrafluoroborate (930 mg, 2.90 mmol) is added to a mixture of 6-methyl-5-(1-methyl-1H-pyrazol-5-yl)-2-oxo-1-[3-(trifluoromethyl)phenyl]-1,2-dihydropyridine-3-carboxylic acid (1.00 g, 2.65 mmol) in N,N-dimethylformamide (4 mL), and the mixture is stirred at room temperature for 20 min. A solution of (4-methylsulfanylphenyl)-methanamine (410 mg, 2.68 mmol) in N,N-dimethylformamide (4 mL) is added, and the mixture is stirred for 30 min. All volatiles are removed under reduced pressure, and the residue is purified by flash chromatography on silica (gradient dichloromethane to dichloromethane/methanol 98:2). Yield: 1.20 g; ESI mass spectrum [M+H]⁺=513, Retention time HPLC: 1.49 min (V003_003).

Intermediate 14

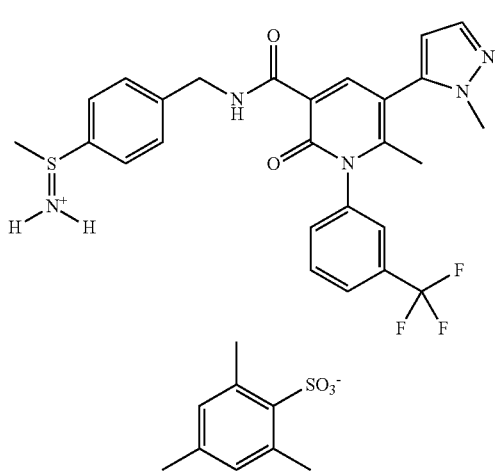

[Methyl-[4-[[[6-methyl-5-(2-methylpyrazol-3-yl)-2-oxo-1-[3-(trifluoromethyl)phenyl]-pyridine-3-carbonyl]amino]methyl]phenyl]-λ⁴-sulfanylidene]ammonium mesitylenesulfonate Step 1

O-Mesitylsulfonylhydroxylamine

A solution of ethyl O-mesitylsulfonylacetohydroxamate (100 mg, 343 µmol) in 1,4-dioxane (0.5 mL) is cooled in an ice bath at 0° C. and treated with concentrated sulfuric acid (70 µL, 1.2 mmol). The mixture is stirred at room temperature for 30 min, diluted with water (7.0 mL) and extracted with dichloromethane (4.0 mL). The phases are separated and the organic layer is used directly in the next step.

Step 2

[Methyl-[4-[[[6-methyl-5-(2-methylpyrazol-3-yl)-2-oxo-1-[3-(trifluoromethyl)phenyl]-pyridine-3-carbonyl]amino]methyl]phenyl]-λ⁴-sulfanylidene]ammonium mesitylenesulfonate A solution of 6-methyl-5-(2-methylpyrazol-3-yl)-N-[(4-methylsulfanylphenyl)methyl]-2-oxo-1-[3-(trifluoromethyl)phenyl]pyridine-3-carboxamide (intermediate 13, 100 mg, 195 µmol) in dichloromethane (2.0 mL) is cooled at 0° C. in an ice bath and treated with O-Mesitylsulfonylhydroxylamine (step 1, 0.86 M in dichloromethane, 2 mL, 172 µmol). The mixture is warmed at room temperature and stirred for 2 h. A second portion of O-mesitylsulfonylhydroxylamine (step 1, 0.86 µM in dichloromethane, 1 mL, 86 µmol) is added, and the mixture is stirred for 1 h. A third portion of O-mesityl-sulfonylhydroxylamine (0.86 µM, 1 mL, 86 µmol) is added, and the mixture is stirred for 20 min. Half of the dichloromethane is removed under reduced pressure, and diethyl ether (2 mL) is added. The precipitate is filtered and dried. Yield: 64 mg; ESI mass spectrum [M+H]⁺=528, Retention time HPLC: 0.74 min (Z012_S04).

Intermediate 15

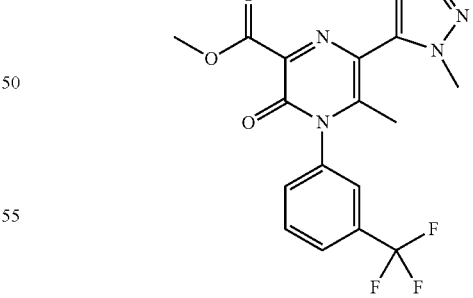

Methyl 5-Methyl-6-(2-methylpyrazol-3-yl)-3-oxo-4-[3-(trifluoromethyl)phenyl]-pyrazine-2-carboxylate A mixture of methyl 6-bromo-5-methyl-3-oxo-4-[3-(trifluoromethyl)phenyl]pyrazine-2-carboxylate (300 mg, 767 µmol), 1-methyl-5-(4,4,5,5-tetramethyl-1,3,2-dioxaborolan-2-yl)pyrazole (240 mg, 1.15 mmol), bis(tri-tert-butylphosphine)palladium(0) (59 mg, 115 μmol) and cesium carbonate (750 mg, 2.30 mmol) in 1,2-dimethoxyethane (4.0 mL) is heated at 110° C. for 10 min and concentrated under reduced pressure. The residue is purified by reversed phase HPLC (Waters SunFire™-$C_{18}$, gradient of acetonitrile in water, 0.1% TFA). Yield: 115 mg; ESI mass spectrum [M+H]$^+$=393; Retention time HPLC: 0.96 min (Z018_S04).

SYNTHESES OF EXAMPLES

Example 1

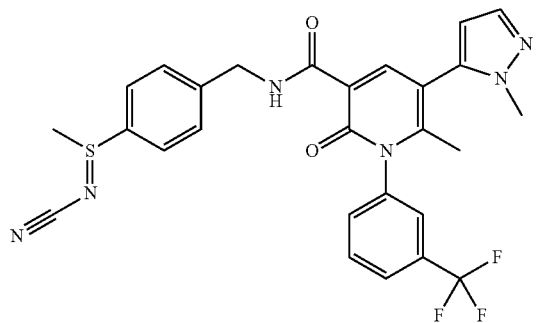 [SMILES: Cc1c(-c2ccnn2C)cc(C(=O)NCc2ccc(/S(C)=N/C#N)cc2)c(=O)n1-c1cccc(C(F)(F)F)c1]

N-[[4-(N-Cyano-S-methyl-sulfinimidoyl)phenyl] methyl]-6-methyl-5-(2-methyl-pyrazol-3-yl)-2-oxo-1-[3-(trifluoromethyl)phenyl]pyridine-3-carboxamide Step 1

[[4-(Aminomethyl)phenyl]-methyl-λ$^4$-sulfanylidene] cyanamide

A mixture of [[4-[(1,3-dioxoisoindolin-2-yl)methyl]phenyl]-methyl-λ$^4$-sulfanylidene]-cyanamide (intermediate 2, 100 mg, 0.31 mmol) and ethanol (2 mL) is treated with hydrazine (80% in water, 60 μL, 0.9 mmol), stirred at room temperature for 30 min and heated at reflux for 45 min. All volatiles are removed under reduced pressure, and the residue is extracted twice with dichloromethane. The combined organic layers are filtered, and the filtrate is concentrated under reduced pressure. Yield: 55 mg.

Step 2

N-[[4-(N-Cyano-S-methyl-sulfinimidoyl)phenyl] methyl]-6-methyl-5-(2-methylpyrazol-3-yl)-2-oxo-1-[3-(trifluoromethyl)phenyl]pyridine-3-carboxamide N,N-Diisopropylethylamine (95 μL, 0.55 mmol) and N,N,N',N'-tetramethyl-O-(benzotriazol-1-yl)uronium tetrafluoroborate (127 mg, 0.40 mmol) is added to a mixture of 6-methyl-5-(2-methylpyrazol-3-yl)-2-oxo-1-[3-(trifluoromethyl) phenyl]pyridine-3-carboxylic acid (115 mg, 0.31 mmol) in N,N-dimethylformamide (2.0 mL), and the mixture is stirred at room temperature for 10 min. A solution of [[4-(aminomethyl)phenyl]-methyl-λ$^4$-sulfanylidene]cyanamide (step 1, 55 mg, 0.23 mmol based on 80% purity) in N,N-dimethylformamide (1.0 mL) is added, and the mixture is stirred for 1 h. All volatiles are removed under reduced pressure, and the residue is purified by reversed phase HPLC (Waters Xbridge™-$C_{18}$, gradient of methanol in water, 0.1% NH$_3$). Yield: 27 mg; ESI mass spectrum [M+H]$^+$=553, Retention time HPLC: 0.65 min (X001_004).

Examples 1.1-1.3

The following examples of Table 1 are prepared in analogy to N-[[4-(N-cyano-S-methyl-sulfinimidoyl)phenyl]methyl]-6-methyl-5-(2-methylpyrazol-3-yl)-2-oxo-1-[3-(trifluoromethyl)phenyl]pyridine-3-carboxamide (example 1), replacing [[4-[(1,3-dioxoisoindolin-2-yl)methyl]phenyl]-methyl-λ$^4$-sulfanylidene]cyanamide (intermediate 2) with the appropriate starting material as indicated in the table.

TABLE 1

(I.A)

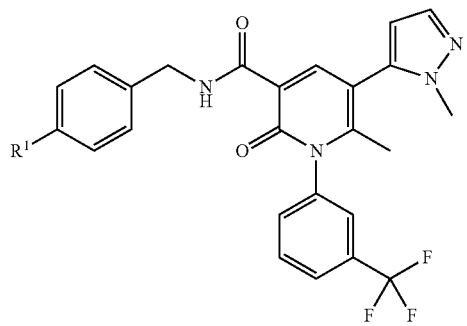

| Example | Starting Material | R$^1$ | MS [M + H]$^+$ | Retention time [min] | HPLC-Method |
|---|---|---|---|---|---|
| 1.1 | Intermediate 9 | 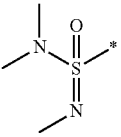 | 587 | 1.26 | Z003_004 |

TABLE 1-continued (I.A)

[Structure of compound I.A shown with R¹ group, pyridine core with methylpyrazole, trifluoromethylphenyl, and benzyl carboxamide substituents]

| Example | Starting Material | R¹ | MS [M + H]⁺ | Retention time [min] | HPLC-Method |
|---|---|---|---|---|---|
| 1.2 | Intermediate 10 | [benzyl-NH-S(=O)(=N-methyl)- group] | 649 | 1.20 | Z002_006 |
| 1.3 | Intermediate 12 | [methoxy-N(methyl)-S(=O)(=N-methyl)- group] | 603 | 1.30 | Z003_004 |

Example 2

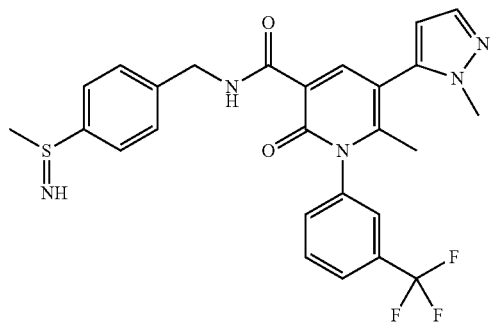 [SMILES: Cc1c(-c2ccnn2C)cc(C(=O)NCc2ccc(S(C)=N)cc2)c(=O)n1-c1cccc(C(F)(F)F)c1]

6-Methyl-5-(2-methylpyrazol-3-yl)-N-[[4-(methylsulfinimidoyl)phenyl]methyl]-2-oxo-1-[3-(trifluoromethyl)phenyl]pyridine-3-carboxamide A solution of N-[[4-(N-cyano-S-methyl-sulfinimidoyl) phenyl]methyl]-6-methyl-5-(2-methylpyrazol-3-yl)-2-oxo-1-[3-(trifluoromethyl)phenyl]pyridine-3-carboxamide (example 1, 38 mg, 69 mol) in dichloromethane (2.0 mL) is cooled at 0° C. and treated with trifluoroacetic anhydride (28 µL, 42 mg, 0.20 mmol). The mixture is stirred at 0° C. for 1 h and warmed at room temperature. All volatiles are removed under reduced pressure, and the residue is dissolved in methanol (1.0 mL). Potassium carbonate (47 mg, 0.34 mmol) is added, and the mixture is stirred at room temperature over night. All volatiles are removed under reduced pressure, and the residue is purified by reversed phase HPLC (Waters Xbridge™-C₁₈, gradient of methanol in water, 0.1% TFA). Yield: 12 mg; ESI mass spectrum [M+H]⁺=528, Retention time HPLC: 0.59 min (X001_004).

Example 3

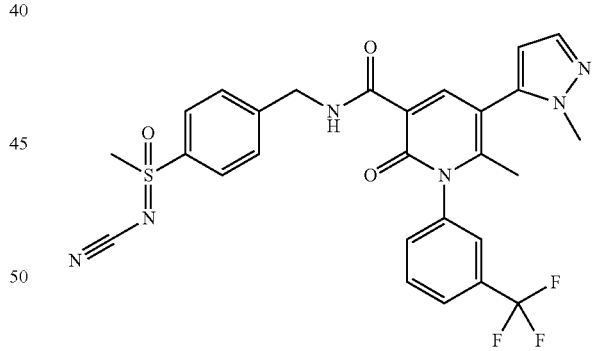

N-[[4-(N-Cyano-S-methyl-sulfonimidoyl)phenyl] methyl]-6-methyl-5-(2-methylpyrazol-3-yl)-2-oxo-1-[3-(trifluoromethyl)phenyl]pyridine-3-carboxamide N,N-Diisopropylethylamine (2.15 mL, 12.5 mmol) and N,N,N',N'-tetramethyl-O-(benzotriazol-1-yl)uronium tetrafluoroborate (2.89 g, 9.01 mmol) is added to a mixture of 6-methyl-5-(2-methylpyrazol-3-yl)-2-oxo-1-[3-(trifluoromethyl)phenyl]pyridine-3-carboxylic acid (2.61 g, 6.93 mmol) in N,N-dimethylformamide (50.0 mL), and the mixture is stirred at room temperature for 10 min. A solution of [[4-(aminomethyl)phenyl]-methyl-oxo-λ⁶-sulfanylidene]cyanamide (intermediate 4, 1.35 g, 5.17 mmol based on 80% purity) in N,N-dimethylformamide (10 mL) is added, and the mixture is stirred for 1 h. All volatiles are removed under reduced pressure, and the residue is purified by flash chromatography on silica (gradient cyclohexane/ethyl acetate 3:7 to ethyl acetate to ethyl acetate/methanol 9:1). Yield: 1.63 g; ESI mass spectrum [M+H]$^+$=569, Retention time HPLC: 1.28 min (V003_003).

Examples 3A and 3B

Enantiomers of Example 3

The enantiomers of racemic N-[[4-(N-cyano-S-methyl-sulfonimidoyl)phenyl]methyl]-6-methyl-5-(2-methylpyrazol-3-yl)-2-oxo-1-[3-(trifluoromethyl)phenyl]pyridine-3-carboxamide (example 3, 30 mg, 53 μmol) are separated by preparative supercritical fluid chromatography on a chiral phase (Daicel Chiralpak IC, 2×10 mm×250 mm, 5 μm, 45% MeOH+0.2% diethylamine in supercritical CO$_2$, 40° C., 120 bar back pressure).

Example 3A

Yield: 11 mg; ESI mass spectrum [M+H]$^+$=569; Retention time: 4.57 min (early eluting enantiomer) (I_IC_40_MeOH_DEA).

Example 3B

Yield: 10 mg; ESI mass spectrum [M+H]$^+$=569; Retention time: 5.04 min (late eluting enantiomer) (I_IC_40_MeOH_DEA).

Example 4

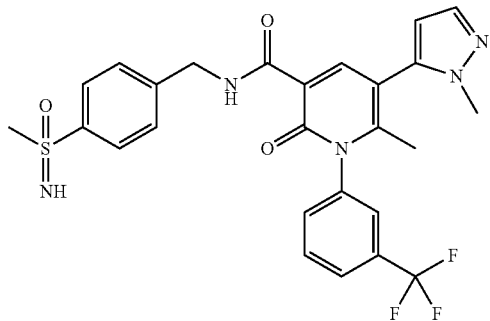 [SMILES: Cc1c(-c2ccnn2C)cc(C(=O)NCc2ccc(S(C)(=N)=O)cc2)c(=O)n1-c1cccc(C(F)(F)F)c1]

6-Methyl-5-(2-methylpyrazol-3-yl)-N-[[4-(methyl-sulfonimidoyl)phenyl]methyl]-2-oxo-1-[3-(trifluoromethyl)phenyl]pyridine-3-carboxamide A solution of N-[[4-(N-cyano-S-methyl-sulfonimidoyl)phenyl]methyl]-6-methyl-5-(2-methylpyrazol-3-yl)-2-oxo-1-[3-(trifluoromethyl)phenyl]pyridine-3-carboxamide (example 3, 100 mg, 176 μmol) in dichloromethane (4 mL) is cooled at 0° C. and treated with trifluoroacetic anhydride (73 μL, 110 mg, 0.52 mmol). The mixture is stirred at 0° C. for 1 h and warmed at room temperature. All volatiles are removed under reduced pressure, and the residue is dissolved in methanol (2.0 mL). Potassium carbonate (122 mg, 0.88 mmol) is added, and the mixture is stirred at room temperature for 2 h. All volatiles are removed under reduced pressure, and the residue is purified by reversed phase HPLC (Waters Xbridge™-C$_{18}$, gradient of methanol in water, 0.1% TFA). Yield: 47 mg; ESI mass spectrum [M+H]$^+$=544, Retention time HPLC: 1.27 min (V003_003).

Examples 4A and 4B

Enantiomers of Example 4

The enantiomers of racemic 6-methyl-5-(2-methylpyrazol-3-yl)-N-[[4-(methylsulfonimidoyl)phenyl]methyl]-2-oxo-1-[3-(trifluoromethyl)phenyl]pyridine-3-carboxamide (example 4, 45 mg, 83 μmol) are separated by preparative supercritical fluid chromatography on a chiral phase (Daicel Chiralpak IC, 2×10 mm×250 mm, 5 μm, 50% MeOH+0.2% diethylamine in supercritical CO$_2$, 40° C., 120 bar back pressure).

Example 4A

Yield: 14 mg; ESI mass spectrum [M+H]$^+$=544; Retention time: 3.98 min (early eluting enantiomer) (I_IC_50_MeOH_DEA).

Example 4B

Yield: 14 mg; ESI mass spectrum [M+H]$^+$=544; Retention time: 4.69 min (late eluting enantiomer) (I_IC_50_MeOH_DEA).

Example 5

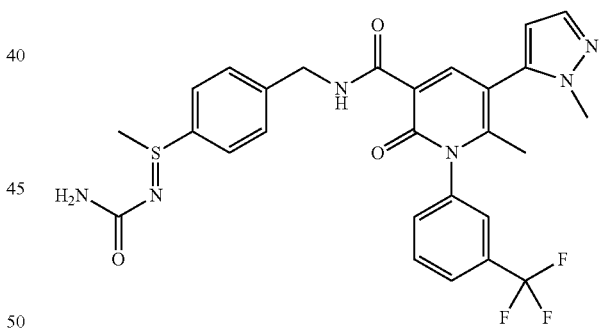

N-[[4-(N-Carbamoyl-S-methyl-sulfinimidoyl)phenyl]methyl]-6-methyl-5-(2-methyl-pyrazol-3-yl)-2-oxo-1-[3-(trifluoromethyl)phenyl]pyridine-3-carboxamide A mixture of N-[[4-(N-cyano-S-methyl-sulfinimidoyl)phenyl]methyl]-6-methyl-5-(2-methylpyrazol-3-yl)-2-oxo-1-[3-(trifluoromethyl)phenyl]pyridine-3-carboxamide (example 1, 50 mg, 90 μmol) and dichloromethane (1.0 mL) is treated with trifluoroacetic acid (20 μL, 30 mg, 260 mmol) and stirred at room temperature for 2 h. All volatiles are removed under reduced pressure, and the residue is treated with a mixture of methanol and water and purified by reversed phase HPLC (Waters Xbridge™-C$_{18}$, gradient of methanol in water, 0.1% TFA). Yield: 25 mg; ESI mass spectrum [M+H]$^+$=571, Retention time HPLC: 0.59 min (X001_004).

Example 6

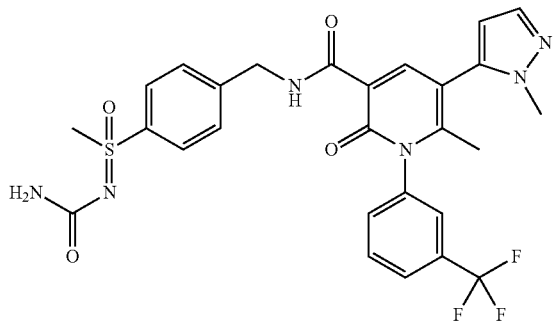 [SMILES: Cc1c(-c2ccnn2C)cc(C(=O)NCc2ccc(S(C)(=O)=NC(N)=O)cc2)c(=O)n1-c1cccc(C(F)(F)F)c1]

N-[[4-(N-Carbamoyl-S-methyl-sulfonimidoyl)phenyl]methyl]-6-methyl-5-(2-methyl-pyrazol-3-yl)-2-oxo-1-[3-(trifluoromethyl)phenyl]pyridine-3-carboxamide The title compound is prepared in analogy to N-[[4-(N-carbamoyl-S-methyl-sulfinimidoyl)-phenyl]methyl]-6-methyl-5-(2-methylpyrazol-3-yl)-2-oxo-1-[3-(trifluoromethyl)phenyl]-pyridine-3-carboxamide (example 5), using N-[[4-(N-cyano-S-methyl-sulfonimidoyl)-phenyl]methyl]-6-methyl-5-(2-methylpyrazol-3-yl)-2-oxo-1-[3-(trifluoromethyl)phenyl]-pyridine-3-carboxamide (example 3, 50 mg, 88 µmol) as starting material. Yield: 5 mg; ESI mass spectrum [M+H]$^+$=587, Retention time HPLC: 0.64 min (X001_004).

Example 7

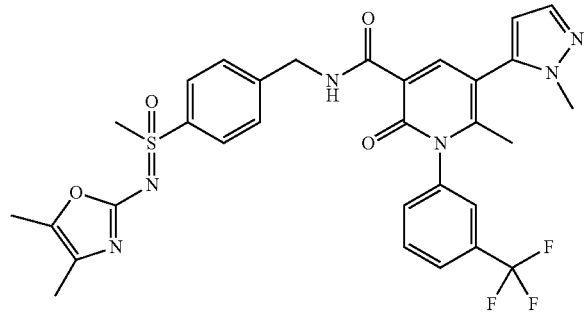 [SMILES: Cc1nc(N=S(C)(=O)c2ccc(CNC(=O)c3cc(-c4ccnn4C)c(C)n(-c4cccc(C(F)(F)F)c4)c3=O)cc2)oc1C]

N-[[4-[N-(4,5-Dimethyloxazol-2-yl)-S-methyl-sulfonimidoyl]phenyl]methyl]-6-methyl-5-(2-methylpyrazol-3-yl)-2-oxo-1-[3-(trifluoromethyl)phenyl] pyridine-3-carboxamide A mixture of N-[[4-(N-cyano-S-methyl-sulfonimidoyl)phenyl]methyl]-6-methyl-5-(2-methylpyrazol-3-yl)-2-oxo-1-[3-(trifluoromethyl)phenyl]pyridine-3-carboxamide (example 3, 172 mg, 0.30 mmol), 3-hydroxy-2-butanon (267 mg, 3.03 mmol) and concentrated hydrochloric acid (3 drops) is stirred at room temperature for 3 h. All volatiles are removed under reduced pressure, and the residue is purified by reversed phase HPLC (Waters Xbridge™-C$_{18}$, gradient of methanol in water, 0.1% NH$_3$). Yield: 12 mg; ESI mass spectrum [M+H]$^+$=639, Retention time HPLC: 0.66 min (X001_004).

Example 8

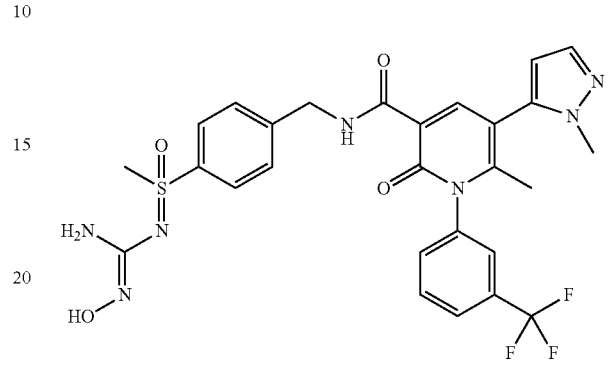

N-[[4-[N—[N-Hydroxycarbamimidoyl]-S-methylsulfonimidoyl]phenyl]methyl]-6-methyl-5-(2-methylpyrazol-3-yl)-2-oxo-1-[3-(trifluoromethyl)phenyl] pyridine-3-carboxamide A solution of hydroxylamine hydrochloride (12 mg, 0.17 mmol) and sodium carbonate (28 mg, 0.26 mmol) in water (100 µL) is added to a solution of N-[[4-(N-cyano-S-methyl-sulfonimidoyl)phenyl]methyl]-6-methyl-5-(2-methylpyrazol-3-yl)-2-oxo-1-[3-(trifluoromethyl)phenyl]pyridine-3-carboxamide (example 3, 50 mg, 88 µmol) in ethanol (300 µL).

The mixture is heated at reflux for 20 min, cooled at room temperature and concentrated under reduced pressure. Water is added, and the mixture is extracted twice with dichloromethane. The combined organic layers are concentrated under reduced pressure, and the residue is purified by reversed phase HPLC (Waters Xbridge™-C$_{18}$, gradient of methanol in water, 0.1% TFA). Yield: 16 mg; ESI mass spectrum [M+H]$^+$=602, Retention time HPLC: 0.60 min (X001_004).

Example 9

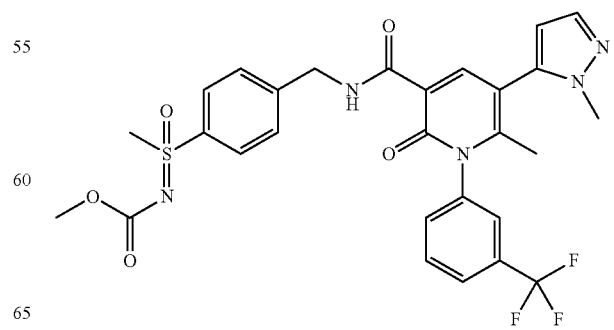

Methyl N-[Methyl-[4-[[[6-methyl-5-(2-methylpyrazol-3-yl)-2-oxo-1-[3-(trifluoromethyl)phenyl]pyridine-3-carbonyl]amino]methyl]phenyl]-oxo-λ⁶-sulfanylidene]-carbamate Pyridine (8 μL, 8 mg, 0.10 mmol) and methyl chloroformate (10 mg, 12 mg, 0.12 mmol) is added to a solution of 6-methyl-5-(2-methylpyrazol-3-yl)-N-[[4-(methylsulfonimidoyl)-phenyl]methyl]-2-oxo-1-[3-(trifluoromethyl)phenyl]pyridine-3-carboxamide (example 4, 50 mg, 92 μmol) in dichloromethane (500 μL), and the mixture is stirred at room temperature for 3 h. Water is added, and the mixture is extracted twice with dichloromethane. The combined organic layers are concentrated under reduced pressure, and the residue is purified by reversed phase HPLC (Waters SunFire™-C₁₈, gradient of acetonitrile in water, 0.1% TFA). Yield: 23 mg; ESI mass spectrum [M+H]⁺=602; Retention time HPLC: 1.19 min (Z002_006).

Examples 9.1-9.3

The following examples of Table 2 are prepared in analogy to methyl N-[methyl-[4-[[[6-methyl-5-(2-methylpyrazol-3-yl)-2-oxo-1-[3-(trifluoromethyl)phenyl]pyridine-3-carbonyl]amino]methyl]phenyl]-oxo-λ⁶-sulfanylidene]carbamate (example 9), replacing methyl chloroformate with the appropriate reagent.

TABLE 2

| Example | R¹ | MS [M + H]⁺ | Retention time [min] | HPLC-Method |
|---|---|---|---|---|
| 9.1 | (acetyl sulfonimidoyl) | 586 | 0.66 | X001_004 |
| 9.2 | (morpholinocarbonyl sulfonimidoyl) | 657 | 1.20 | Z002_006 |
| 9.3 | (MeO₂S-N sulfonimidoyl) | 622 | 0.65 | X001_004 |

Example 10

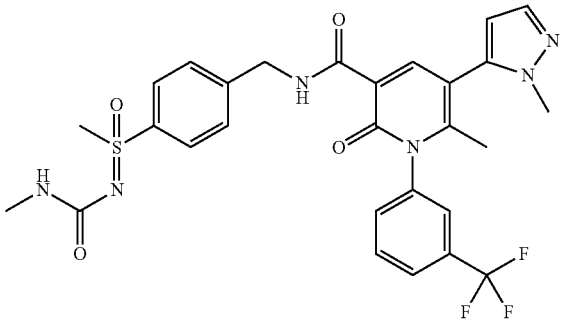 [SMILES: CNC(=O)N=S(C)(=O)c1ccc(CNC(=O)c2cc(-c3ccnn3C)c(C)n(-c3cccc(C(F)(F)F)c3)c2=O)cc1]

6-Methyl-N-[[4-[S-methyl-N-(methylcarbamoyl)sulfonimidoyl]phenyl]methyl]-5-(2-methylpyrazol-3-yl)-2-oxo-1-[3-(trifluoromethyl)phenyl]pyridine-3-carboxamide A mixture of 6-methyl-5-(2-methylpyrazol-3-yl)-N-[[4-(methylsulfonimidoyl)phenyl]-methyl]-2-oxo-1-[3-(trifluoromethyl)phenyl]pyridine-3-carboxamide (example 4, 50 mg, 92 μmol) and methylisocyanate (5 μL, 5 mg, 90 μmol) in dichloromethane (1 mL) is stirred at room temperature for 2 days. Water is added, and the mixture is extracted with dichloromethane. The combined organic layers are concentrated under reduced pressure, and the residue is purified by reversed phase HPLC (Waters Xbridge™-C₁₈, gradient of acetonitrile in water, 0.1% TFA). Yield: 17 mg; ESI mass spectrum [M+H]⁺=601, Retention time HPLC: 0.54 min (X012_S01).

Example 11

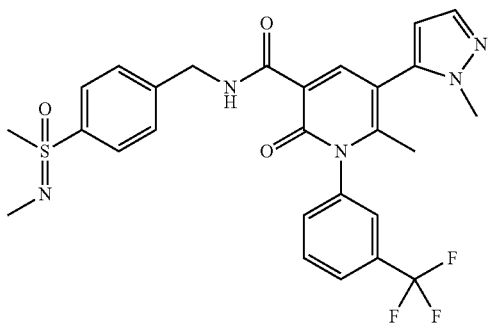 [SMILES: CN=S(C)(=O)c1ccc(CNC(=O)c2cc(-c3ccnn3C)c(C)n(-c3cccc(C(F)(F)F)c3)c2=O)cc1]

N-[[4-(N,S-Dimethylsulfonimidoyl)phenyl]methyl]-6-methyl-5-(2-methylpyrazol-3-yl)-2-oxo-1-[3-(trifluoromethyl)phenyl]pyridine-3-carboxamide Under an atmosphere of argon, a mixture of 6-methyl-5-(2-methylpyrazol-3-yl)-N-[[4-(methylsulfonimidoyl)phenyl]methyl]-2-oxo-1-[3-(trifluoromethyl)phenyl]pyridine-3-carboxamide (example 4, 54 mg, 0.10 mmol) and paraformaldehyde (18 mg, 0.20 mmol) in formic acid (1.4 mL) is heated at 100° C. over night and cooled at room temperature. All volatiles are removed under reduced pressure, and the residue is purified by reversed phase HPLC (Waters Xbridge™-$C_{18}$, gradient of acetonitrile in water, 0.1% $NH_3$). Yield: 7 mg; ESI mass spectrum $[M+H]^+$=558, Retention time HPLC: 1.00 min (V011_S01).

Example 12

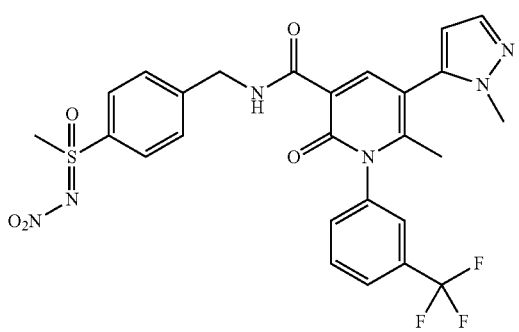 [SMILES: Cc1c(-c2ccnn2C)cc(C(=O)NCc2ccc(S(C)(=O)=N[N+](=O)[O-])cc2)c(=O)n1-c1cccc(C(F)(F)F)c1]

6-Methyl-N-[[4-(S-methyl-N-nitro-sulfonimidoyl) phenyl]methyl]-5-(2-methylpyrazol-3-yl)-2-oxo-1-[3-(trifluoromethyl)phenyl]pyridine-3-carboxamide

Step 1

N-[[4-(Aminomethyl)phenyl]-methyl-oxo-$\lambda^6$-sulfanylidene]nitramide

A solution of N-[[4-[(1,3-dioxoisoindolin-2-yl)methyl]phenyl]-methyl-oxo-$\lambda^6$-sulfanylidene]nitramide (intermediate 6, 120 mg, 0.33 mmol) in a mixture of acetonitrile (2 mL), tetrahydrofuran (1 mL) and ethanol (1 mL) is treated with 1,2-diaminoethane (38 μL, 34 mg, 0.57 mmol), and the mixture is heated at 60° C. for 7 h. All volatiles are removed under reduced pressure, and the residue is treated with dichloromethane. The mixture is filtered, and the filtrate is reduced under reduced pressure. Yield: 69 mg.

Step 2

6-Methyl-N-[[4-(S-methyl-N-nitro-sulfonimidoyl) phenyl]methyl]-5-(2-methylpyrazol-3-yl)-2-oxo-1-[3-(trifluoromethyl)phenyl]pyridine-3-carboxamide N,N-Diisopropylethylamine (93 μL, 0.54 mmol) and N,N,N',N'-tetramethyl-O-(benzotriazol-1-yl)uronium tetrafluoroborate (125 mg, 0.39 mmol) is added to a mixture of 6-methyl-5-(2-methylpyrazol-3-yl)-2-oxo-1-[3-(trifluoromethyl)phenyl]pyridine-3-carboxylic acid (114 mg, 0.30 mmol) in N,N-dimethylformamide (1.5 mL), and the mixture is stirred at room temperature for 10 min. A solution of N-[[4-(aminomethyl)phenyl]-methyl-oxo-$\lambda^6$-sulfanylidene]nitramide (step 1, 69 mg, 0.24 mmol based on 80% purity) in N,N-dimethylformamide (0.5 mL) is added, and the mixture is stirred for 1 h. Water is added, and the mixture is extracted twice with dichloromethane. The organic layers are combined and concentrated under reduced pressure, and the residue is purified by reversed phase HPLC (Waters Xbridge™-$C_{18}$, gradient of acetonitrile in water, 0.1% $NH_3$). Yield: 31 mg; ESI mass spectrum $[M+H]^+$=589, Retention time HPLC: 0.60 min (X012_S01).

Example 13

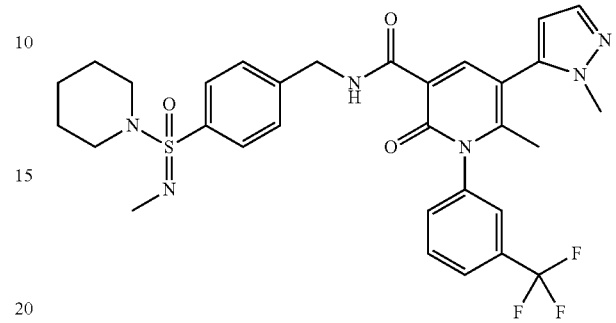

6-Methyl-N-[[4-[N-methyl-S-(1-piperidyl)sulfonimidoyl]phenyl]methyl]-5-(2-methyl-pyrazol-3-yl)-2-oxo-1-[3-(trifluoromethyl)phenyl]pyridine-3-carboxamide

Step 1

[4-[N-Methyl-S-(1-piperidyl)sulfonimidoyl]phenyl] methanamine

Tert-butyl hypochlorite (40 μL, 38 mg, 0.35 mmol) is added to a mixture of 4-[(1,3-dioxoisoindolin-2-yl)methyl]-N-methyl-benzenesulfinamide (intermediate 8, 96 mg, 0.30 mmol) in tetrahydrofuran (2.0 mL), and the mixture is stirred for 5 min. Piperidine (120 μL, 103 mg, 1.2 mmol) is added and the mixture is stirred at room temperature for 2 h. The mixture is concentrated under reduced pressure, and the residue is dissolved in ethanol (2 mL). Hydrazine (80% in water, 120 μL, 2.5 mmol) is added, and the mixture is heated at reflux for 1.5 h. All volatiles are removed under reduced pressure, and the residue is dissolved in N,N-dimethylformamide (0.5 mL) to give solution A.

Step 2

6-Methyl-N-[[4-[N-methyl-S-(1-piperidyl)sulfonimidoyl]phenyl]methyl]-5-(2-methyl-pyrazol-3-yl)-2-oxo-1-[3-(trifluoromethyl)phenyl]pyridine-3-carboxamide N,N-Diisopropylethylamine (80 μL, 0.62 mmol) and N,N,N',N'-tetramethyl-O-(benzotriazol-1-yl)uronium tetrafluoroborate (144 mg, 0.45 mmol) is added to a mixture of 6-methyl-5-(2-methylpyrazol-3-yl)-2-oxo-1-[3-(trifluoromethyl)phenyl]pyridine-3-carboxylic acid (130 mg, 345 μmol) in N,N-dimethylformamide (1 mL), and the mixture is stirred at room temperature for 15 min. A solution of [4-[N-methyl-S-(1-piperidyl)-sulfonimidoyl]phenyl]methanamine in N,N-dimethylformamide (solution A, step 1) is added, and the mixture is stirred for 6 h. Water is added, and the mixture is extracted twice with ethyl acetate. The organic layers are combined and concentrated under reduced pressure, and the residue is purified by reversed phase HPLC (Waters Xbridge™-$C_{18}$, gradient of acetonitrile in water, 0.1% $NH_3$).

Yield: 7 mg; ESI mass spectrum [M+H]$^+$=627, Retention time HPLC: 1.35 min (Z003_004)

Example 14

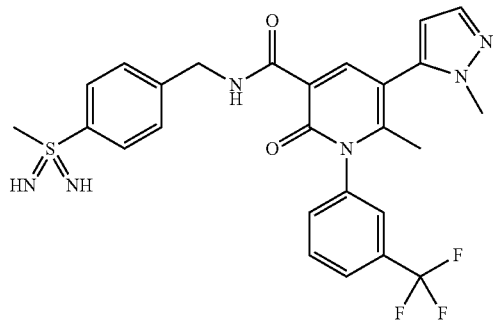 [SMILES: Cc1c(-c2ccnn2C)cc(C(=O)NCc2ccc(S(C)(=N)=N)cc2)c(=O)n1-c1cccc(C(F)(F)F)c1]

6-Methyl-5-(2-methylpyrazol-3-yl)-N-[[4-(methyl-sulfonodiimidoyl)phenyl]methyl]-2-oxo-1-[3-(trifluoromethyl)phenyl]pyridine-3-carboxamide A solution of 6-methyl-5-(2-methylpyrazol-3-yl)-N-[(4-methylsulfanylphenyl)methyl]-2-oxo-1-[3-(trifluoromethyl)phenyl]pyridine-3-carboxamide (intermediate 13, 1.20 g, 2.34 mmol) in acetonitrile (6 mL) is cooled at −40° C. Ammonia (0.8 g, 47 mmol) is condensed into the reaction mixture, and the mixture is cooled at −50° C. A solution of tert-butyl hypochlorite (1.27 g, 1.22 g, 11.2 mmol) in acetonitrile (1 mL) is added dropwise while the temperature is kept below −45° C. Another portion of ammonia (0.4 g, 23 mmol) is condensed into the mixture, and the mixture is stirred at −50° C. over night. The mixture is warmed at room temperature and filtered. The filtrate is concentrated under reduced pressure, and the residue is purified by flash chromatography on silica (gradient dichloromethane to dichloromethane/methanol 9:1). Yield: 190 mg; ESI mass spectrum [M+H]$^+$=543, Retention time HPLC: 0.94 min (V012_S01).

Example 15

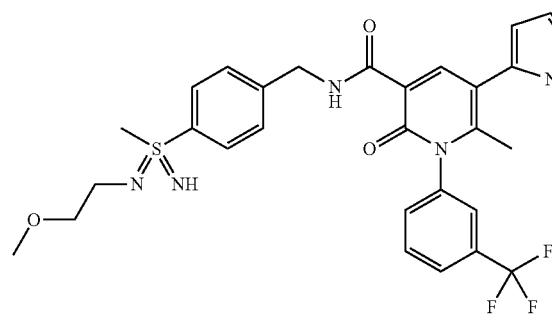

N-[[4-[N-(2-Methoxyethyl)-S-methyl-sulfonodiimidoyl]phenyl]methyl]-6-methyl-5-(2-methylpyrazol-3-yl)-2-oxo-1-[3-(trifluoromethyl)phenyl]pyridine-3-carboxamide Under an atmosphere of argon, sodium carbonate (43 mg, 0.41 mmol) and N-chlorosuccinimide (50 mg, 0.37 mmol) is added at 0° C. to a solution of [methyl-[4-[[[6-methyl-5-(2-methylpyrazol-3-yl)-2-oxo-1-[3-(trifluoromethyl)phenyl]pyridine-3-carbonyl]amino]-methyl]phenyl]-λ$^4$-sulfanylidene]ammonium mesitylenesulfonate (intermediate 14, 246 mg, 338 μmol) in N,N-dimethylformamide (5.0 mL), and the mixture is stirred at 0° C. for 15 min. 2-Methoxyethylamine (89 μL, 76 mg, 1.02 mmol) is added, and the mixture is warmed at room temperature and stirred over night. Water is added, and the mixture is extracted twice with dichloromethane. The combined organic layers are concentrated under reduced pressure, and the residue is purified by reversed phase HPLC (Waters Xbridge™-C$_{18}$, gradient of acetonitrile in water, 0.1% NH$_3$). Yield: 42 mg; ESI mass spectrum [M+H]$^+$=601, Retention time HPLC: 1.16 min (Z003_004).

Examples 15.1-15.2

The following examples of Table 3 are prepared in analogy to N-[[4-[N-(2-methoxyethyl)-S-methyl-sulfonodiimidoyl]phenyl]methyl]-6-methyl-5-(2-methylpyrazol-3-yl)-2-oxo-1-[3-(trifluoromethyl)phenyl]pyridine-3-carboxamide (example 15), replacing 2-methoxy-ethylamine with the appropriate amine as reagent.

TABLE 3

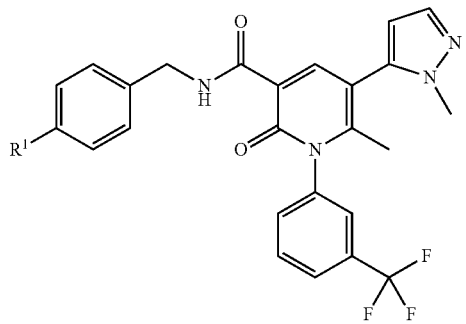

| Example | R$^1$ | MS [M + H]$^+$ | Retention time [min] | HPLC-Method |
|---|---|---|---|---|
| 15.1 | | 557 | 0.48 | X012_S01 |
| 15.2 | | 568 | 0.53 | X012_S01 |

Example 16

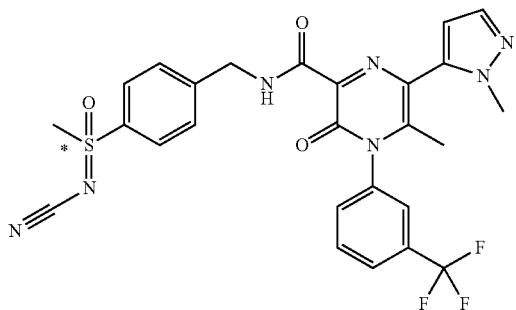 [SMILES: Cc1c(-c2ccnn2C)nc(C(=O)NCc2ccc(S(C)(=O)=NC#N)cc2)c(=O)n1-c1cccc(C(F)(F)F)c1]

N-[[4-(N-Cyano-S-methyl-sulfonimidoyl)phenyl]
methyl]-5-methyl-6-(2-methylpyrazol-3-yl)-3-oxo-4-
[3-(trifluoromethyl)phenyl]pyrazine-2-carboxamide Enantiomerically pure [[4-(aminomethyl)phenyl]-methyl-oxo-$\lambda^6$-sulfanylidene]cyanamide (intermediate 4A, 70 mg, 0.33 mmol) is added to a solution of methyl 5-methyl-6-(2-methylpyrazol-3-yl)-3-oxo-4-[3-(trifluoromethyl)phenyl] pyrazine-2-carboxylate (intermediate 15, 65 mg, 0.17 mmol) in tetrahydrofuran (1.0 mL), and the mixture is stirred at room temperature over night and purified by reversed phase HPLC (Waters SunFire™-$C_{18}$, gradient of acetonitrile in water, 0.1% TFA). Yield: 10 mg; ESI mass spectrum [M+H]$^+$=570; Retention time HPLC: 0.96 min (Z018_S04).

Example 17

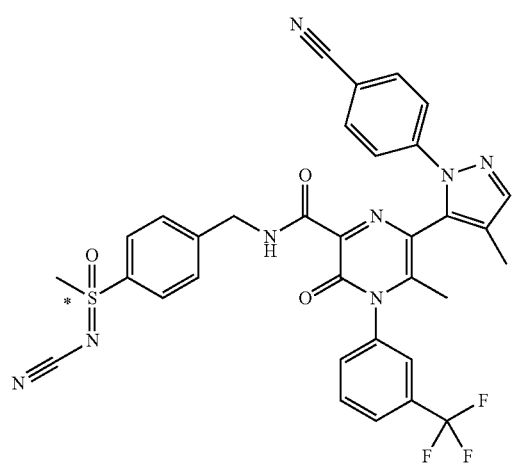 [SMILES: Cc1cnn(-c2ccc(C#N)cc2)c1-c1nc(C(=O)NCc2ccc(S(C)(=O)=NC#N)cc2)c(=O)n(-c2cccc(C(F)(F)F)c2)c1C]

N-[[4-(N-Cyano-S-methyl-sulfonimidoyl)phenyl]
methyl]-6-[2-(4-cyanophenyl)pyrazol-3-yl]-5-me-
thyl-3-oxo-4-[3-(trifluoromethyl)phenyl]pyrazine-2-
carboxamide Enantiomericylla pure [[4-(aminomethyl)phenyl]-methyl-oxo-$\lambda^6$-sulfanylidene]cyanamide (intermediate 4A, 66 mg, 0.32 mmol) is added to a solution of methyl 6-[2-(4-cyanophenyl)pyrazol-3-yl]-5-methyl-3-oxo-4-[3-(trifluoromethyl)phenyl]pyrazine-2-carboxylate (60 mg, 0.13 mmol) in tetrahydrofuran (600 μL), and the mixture is stirred at room temperature over night and purified by reversed phase HPLC (Waters Xbridge™-$C_{18}$, gradient of acetonitrile in water, 0.1% NH$_3$). Yield: 19 mg; ESI mass spectrum [M+H]$^+$=657, Retention time HPLC: 0.80 min (003_CA04).

Pharmacological Data

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: 1-1270). All other materials were of the highest grade commercially available. The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA. Assay conditions: Test compounds were prediluted in DMSO and subsequently in compound buffer (5% DMSO final). 5 μL of these compound dilutions were mixed with 10 μl Neutrophil elastase (9 ng/ml in assay buffer) in a black 384 well OptiPlate (Perkin Elmer, Cat No.: 6007270) and incubated for 15 min at room temperature. Subsequently 10 μL substrate solution in assay buffer were added (250 μM final concentration) and the plates were incubated for 60 min at room temperature. After inactivation of the enzyme, fluorescence intensities were measured at 380 nm excitation and 460 nm emission wavelengths. Each plate contains wells with a high value control (DMSO+enzyme+substrate) and wells with a low value control (DMSO+inactivated enzyme+substrate). IC$_{50}$ values were estimated using a sigmoidal concentration response curve with variable slope. Means of low values were taken as 0%, means of high values as 100%. The IC$_{50}$ values of selected compounds in the Neutrophil Elastase assay are listed in Table 4.

TABLE 4

| Example | IC$_{50}$ [nM] |
| --- | --- |
| 1 | 1.2 |
| 1.1 | 11.4 |
| 1.2 | 14.4 |
| 1.3 | 12.5 |
| 2 | 42.0 |
| 3 | 2.6 |
| 3A | 4.5 |
| 3B | 2.3 |
| 4 | 173.2 |
| 4A | 93.9 |
| 4B | 41.5 |
| 5 | 35.7 |
| 6 | 45.8 |
| 7 | 34.3 |
| 8 | 64.4 |
| 9 | 17.6 |
| 9.1 | 37.0 |
| 9.2 | 72.7 |
| 9.3 | 12.6 |
| 10 | 50.0 |
| 11 | 40.3 |
| 12 | 5.0 |
| 13 | 28.4 |
| 14 | 261.5 |
| 15 | 43.5 |
| 15.1 | 88.7 |
| 15.2 | 6.7 |
| 16 | 11.1 |
| 17 | <1 |

Combinations

The compounds of general formula I may be used on their own or combined with other active substances of formula I according to the invention. The compounds of general formula I may optionally also be combined with other pharmacologically active substances. These include, µ2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors Non-steroidale anti-inflammatory agents (NSAIDs), Cathepsin C (or DPPI/Dipeptidyl-aminopeptidase I) inhibitors, CRTH2 antagonists, DP1-receptor modulators, Thromboxane receptor antagonists, CCR3 antagonists, $CCR^4$ antagonists, $CCR^1$ antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:
  Betamimetics with corticosteroids, PDE4-inhibitors, CRTH2-inhibitors or LTD4-antagonists,
  Anticholinergics with betamimetics, corticosteroids, PDE4-inhibitors, CRTH2-inhibitors or LTD4-antagonists,
  Corticosteroids with PDE4-inhibitors, CRTH2-inhibitors or LTD4-antagonists
  PDE4-inhibitors with CRTH2-inhibitors or LTD4-antagonists
  CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury (ALI) and adult respiratory diseases syndrome (ARDS).

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, *Pneumocystis carnii*, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

1. A compounds of the formula 1

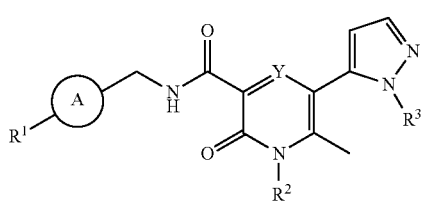

wherein

A is phenyl or a five- or six-membered, aromatic heteroring comprising one, two or three heteroatoms independently selected from the group consisting of N, (O$^-$)—N$^+$, O and S;

$R^1$ is selected from the group consisting of

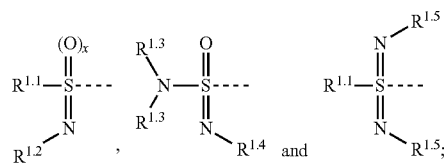

$R^{1.1}$ is $C_{1-4}$-alkyl-, $C_{3-6}$-cycloalkyl- or $C_{1-4}$-haloalkyl-;
$R^{1.2}$ is selected from the group consisting of H, NC—, O$_2$N—, $C_{1-4}$-alkyl-, $C_{3-6}$-cycloalkyl-, $C_{1-4}$-alkyl-(O)C—, $C_{3-6}$-cycloalkyl-(O)C—, H$_2$N—(O)C—, $C_{1-4}$-alkyl-NH—(O)C—, $C_{3-6}$-cycloalkyl-NH—(O)C—, $C_{1-4}$-alkyl-O—(O)C—, $C_{3-6}$-cycloalkyl-O—(O)C—, H$_2$N—(HO—N)C—, morpholinyl-(O)C— and $C_{1-4}$-alkyl-SO$_2$—,
or a 5-membered aromatic heterocycle containing one, two or three atoms selected from the group consisting of N, O and S; each ring optionally substituted with one or two residues selected independently from each other from the group consisting of $C_{1-4}$-alkyl-, $C_{3-6}$-cycloalkyl-, halogen and $C_{1-4}$-haloalkyl-;
$R^{1.3}$ is selected from the group consisting of H, $C_{1-4}$-alkyl-, $C_{3-6}$-cycloalkyl-, $C_{1-4}$-alkyl-O—, $C_{3-6}$-cycloalkyl-O—, benzyl-, H$_2$N—, $C_{1-4}$-alkyl-NH— and $(C_{1-4}$-alkyl-$)_2$N—;
or two $R^{1.3}$ are together $C_{2-5}$-alkylene forming a carbocyclic heteroring;
$R^{1.4}$ is $C_{1-4}$-alkyl- or $C_{3-6}$-cycloalkyl-;
$R^{1.5}$ is selected from the group consisting of H, NC—, $C_{1-4}$-alkyl-, $C_{3-6}$-cycloalkyl- and $C_{1-4}$-alkyl-O—$C_{1-4}$-alkyl-;
x is 0 or 1;
$R^2$ is phenyl or pyridyl, each ring optionally substituted with one or two residues selected independently from each other from the group consisting of $C_{1-4}$-alkyl-, halogen and $C_{1-4}$-haloalkyl-;
$R^3$ is selected from the group consisting of $C_{1-4}$-alkyl-, $C_{3-6}$-cycloalkyl-, $C_{1-4}$-haloalkyl- and $C_{1-4}$-alkyl-O—$C_{1-4}$-alkyl-;
or phenyl or pyridyl, each ring optionally substituted with one or two residues selected independently from each other from the group consisting of NC—, halogen, $C_{1-4}$-alkyl- and $C_{1-4}$-haloalkyl-;
Y is CH or N;
or a salt thereof.

2. A compound of the formula 1, according to claim 1, wherein A is phenyl or pyridyl.

3. A compound of the formula 1, according to claim 1, wherein
Y is CH.

4. A compound of the formula 1, according to claim 1, wherein
$R^1$ is

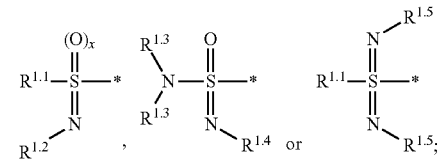

$R^{1.1}$ is selected from the group consisting of $C_{1-4}$-alkyl-, $C_{3-6}$-cycloalkyl- and $C_{1-4}$-haloalkyl-;

$R^{1.2}$ is selected from the group consisting of H, NC—, $O_2N$—, $C_{1-4}$-alkyl-, $C_{3-6}$-cycloalkyl-, $C_{1-4}$-alkyl-(O)C—, $C_{3-6}$-cycloalkyl-(O)C—, $H_2N$—(O)C—, $C_{1-4}$-alkyl-NH—(O)C—, $C_{3-6}$-cycloalkyl-NH—(O)C—, $C_{1-4}$-alkyl-O—(O)C—, $C_{3-6}$-cycloalkyl-O—(O)C—, $H_2N$—(HO—N)C—, morpholinyl-(O)C— and $C_{1-4}$-alkyl-$SO_2$—, or a 5-membered aromatic heterocycle containing one, two or three atoms selected from N, O and S; each ring optionally substituted with one or two residues selected independently from each other from the group consisting of $C_{1-4}$-alkyl-, $C_{3-6}$-cycloalkyl-, halogen and $C_{1-4}$-haloalkyl-;

$R^{1.3}$ is selected from the group consisting of H, $C_{1-4}$-alkyl-, $C_{3-6}$-cycloalkyl-, $C_{1-4}$-alkyl-O—, $C_{3-6}$-cycloalkyl-O—, benzyl-, $H_2N$— and $C_{1-4}$-alkyl-NH—;

or two $R^{1.3}$ are together $C_{2-5}$-alkylene forming a carbocyclic heteroring;

$R^{1.4}$ is $C_{1-4}$-alkyl- or $C_{3-6}$-cycloalkyl-;

$R^{1.5}$ is selected from the group consisting of H, NC—, $C_{1-4}$-alkyl-, $C_{3-6}$-cycloalkyl-, and $C_{1-4}$-alkyl-O—$C_{1-4}$-alkyl-;

x is 0 or 1.

5. A compound of the formula 1, according to claim 1, wherein $R^2$ is phenyl or pyridyl, each ring optionally substituted with one or two residues selected independently from each other from the group consisting of F, $F_2HC$— and $F_3C$—.

6. A compound of the formula 1 according to claim 1, wherein $R^3$ is $C_{1-4}$-alkyl- or phenyl, said phenyl being optionally substituted with one or two residues selected independently from each other from the group consisting of NC—, halogen, $C_{1-4}$-alkyl- and $C_{1-4}$-haloalkyl-.

7. A compound of the formula 1 according to claim 1, wherein

A is phenyl;

$R^1$ is

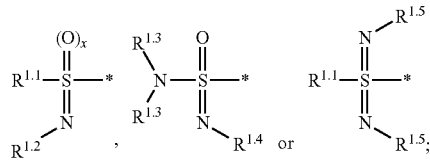

$R^{1.1}$ is methyl;

$R^{1.2}$ is H, NC—, $O_2N$—, methyl, $CH_3$—(O)C—, $H_2N$—(O)C—, $CH_3$—NH—(O)C—, $CH_3$—O—(O)C—, $H_2N$—(HO—N)C—, morpholinyl-(O)C—, $CH_3$—$SO_2$— or 4,5-dimethyloxazol-2-yl;

$R^{1.3}$ H, methyl, $CH_3$—O— or benzyl-; or two $R^{1.3}$ are together form —$(CH_2)_5$—;

$R^{1.4}$ is methyl;

$R^{1.5}$ is H, NC—, methyl or $CH_3$—O—$(CH_2)_2$—;

x is 0 or 1;

$R^2$ is

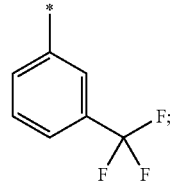 [SMILES: *c1cccc(C(F)(F)F)c1]

$R^3$ is methyl- or 4-cyanophenyl; and

Y is CH or N;

or a pharmaceutically acceptable salt thereof.

8. A method for the treatment of chronic obstructive pulmonary disease which comprises administering to a host suffering from such condition a therapeutically effective amount of a compound of the formula 1 according to claim 1.

9. A pharmaceutical composition comprising a compound of the formula 1 according to claim 1, or a pharmaceutically acceptable salt thereof, and a pharmaceutically acceptable carrier or diluent.

* * * * *